United States Patent
Byrne et al.

(10) Patent No.: US 10,787,684 B2
(45) Date of Patent: Sep. 29, 2020

(54) LARGE GENE EXCISION AND INSERTION

(71) Applicant: President and Fellows of Harvard College, Cambridge, MA (US)

(72) Inventors: Susan M. Byrne, Brookline, MA (US); George M. Church, Brookline, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 0 days.

(21) Appl. No.: 14/319,693

(22) Filed: Jun. 30, 2014

(65) Prior Publication Data

US 2015/0140664 A1     May 21, 2015

Related U.S. Application Data

(60) Provisional application No. 61/906,188, filed on Nov. 19, 2013.

(51) Int. Cl.

| | |
|---|---|
| C12Q 1/68 | (2018.01) |
| C12N 9/14 | (2006.01) |
| C12N 9/22 | (2006.01) |
| C12N 9/52 | (2006.01) |
| C12N 15/00 | (2006.01) |
| C07H 21/02 | (2006.01) |
| C07H 21/04 | (2006.01) |
| A61K 38/43 | (2006.01) |
| C12N 15/90 | (2006.01) |
| C12N 15/10 | (2006.01) |

(52) U.S. Cl.
CPC ......... *C12N 15/907* (2013.01); *C12N 15/102* (2013.01)

(58) Field of Classification Search
None
See application file for complete search history.

(56) References Cited

U.S. PATENT DOCUMENTS

| | | | |
|---|---|---|---|
| 8,697,359 B1 | 4/2014 | Zhang | |
| 2010/0076057 A1 | 3/2010 | Sontheimer et al. | |
| 2011/0189776 A1 | 8/2011 | Terns et al. | |
| 2011/0223638 A1 | 9/2011 | Wiedenheft et al. | |
| 2012/0315670 A1 | 12/2012 | Jacobson et al. | |
| 2013/0130248 A1 | 5/2013 | Haurwitz et al. | |
| 2013/0253040 A1 | 9/2013 | Miller et al. | |
| 2013/0309670 A1* | 11/2013 | Frendewey ............ C12N 15/85 435/6.11 |
| 2014/0068797 A1* | 3/2014 | Doudna et al. ................. 800/18 |
| 2014/0242699 A1* | 8/2014 | Zhang .......................... 435/455 |
| 2014/0342458 A1* | 11/2014 | Mali et al. .................... 435/462 |
| 2014/0356956 A1* | 12/2014 | Church et al. ................ 435/441 |
| 2014/0359795 A1* | 12/2014 | Fahrenkrug et al. ........... 800/13 |

FOREIGN PATENT DOCUMENTS

| | | |
|---|---|---|
| WO | 2008/108989 | 9/2008 |
| WO | 2010/054108 | 5/2010 |
| WO | 2011/143124 | 11/2011 |
| WO | 2012/164565 | 12/2012 |
| WO | 2013/098244 | 7/2013 |
| WO | 2013/126794 A1 | 8/2013 |
| WO | 2013/141680 A1 | 9/2013 |
| WO | 2013/142578 A1 | 9/2013 |
| WO | 2013142578 A1 | 9/2013 |
| WO | 2013/163394 A1 | 10/2013 |
| WO | 2013/176772 | 11/2013 |
| WO | 2013169802 A1 | 11/2013 |
| WO | 2014/022702 A2 | 2/2014 |
| WO | 2014/165825 A2 | 10/2014 |
| WO | 2015/088643 A1 | 6/2015 |

OTHER PUBLICATIONS

Gratz et al. (Genetics, 2013, 194:1029-1035 and 2SI-10S2; published May 24, 2013).*
Ran et al. (Cell, 154:1380-1389, published Aug. 29, 2013).*
Fujii et al. (Nucleic Acid Research, 2013, 41:e187; p. 1-9; published online on Aug. 30, 2013).*
Xiao et al. (Nucleic Acid Research, 2013, 41:e141, p. 1-11; published online on Jun. 6, 2013).*
Gratz et al. (Genetics, 2013, 194:1029-1035; published Aug. 2013).*
Al-Attar et al., Clustered Regularly Interspaced Short Palindromic Repeats (CRISPRs ): The Hallmark of an Ingenious Antiviral Defense Mechanism in Prokaryotes, Bioi Chem. (20 11) vol. 392, Issue 4, pp. 277-289.
Carroll, "A CRISPR Approach to Gene Targeting" 20(9) Molecular Therapy 1658-1660 (Sep. 2012).
Gasiunas et al., "Cas9-crRNA ribonucleoprotein complex mediates specific DNA cleavage for adaptive immunity in bacteria" 109(39) Proceedings of the National Academy of Sciences USA E2579-E2586 (Sep. 4, 2012).
Jinek et aL., "A Programmable Dual-RNA-Guided DNA Endonuclease in Adaptive Bacterial Immunity" 337 Science 816-821 (Aug. 17, 2012).

(Continued)

*Primary Examiner* — Julie Wu
(74) *Attorney, Agent, or Firm* — Banner & Witcoff, Ltd.

(57) ABSTRACT

Methods of simultaneously excising large nucleic acid sequences from a target nucleic acid and inserting large foreign nucleic sequences into the target nucleic acid sequence using DNA binding protein nucleases are described.

34 Claims, 9 Drawing Sheets
Specification includes a Sequence Listing.

(56) References Cited

OTHER PUBLICATIONS

Jinek, et al. 'RNA-programmed genome editing in human cells.' eLite 2013;2:e00471. [retrieved 1-3, 6, 7, 10-12 on Jun. 3, 2014). Retrieved from the Internet. <URL: http://elife.elifesciences.org/content/2/e00471 >. entire document.

Hale et al., Essential Features and Rational Design of CRISPR RNAs That Function With the Cas RAMP Module Complex to Cleave RNAs, Molecular Cell, (20 12) vol. 45, Issue 3, 292-302.

Hatoum-Aslan, et al. 'Mature clustered, regularly interspaced, short palindromic repeats RNA 5,9, 14 (crRNA) length is measured by a ruler mechanism anchored at the precursor processing site.' Proceedings of the National Academy of Sciences. vol. 108, No. 52. pp. 21218-21222. Dec. 2011. entire document.

Makarova et al., "Evolution and classification of the CRISPR-Cas systems" 9(6) Nature Reviews Microbiology 467-477 (1-23) (Jun. 2011).

Roh et al. 'Diverse CRISPRs Evolving in Human Microbiomes.' PLoS Genetics. vol. 8, No. 6. 1-14 pp. 1-12. Jun. 2012. entire document.

Sontheimer Erik, Project 7: Establishing RNA-Directed DNA Targeting in Eukaryotic Cells; Project dates: Nov. 16, 2011 to Dec. 31, 2012 (Feb. 4, 2012).

Wiedenheft et al., "RNA-guided genetic silencing systems in bacteria and archaea" 482 Nature 331-338 (Feb. 16, 2012).

International Search Report and Written Opinion issued in corresponding International Application No. PCT/US14/66324, dated Jun. 15, 2015.

S. M. Byrne et al: "Multi-kilobase homozygous targeted gene replacement in human induced pluripotent stem cells", Nucleic Acids Research, vol. 43, No. 3, Nov. 20, 2014 (Nov. 20, 2014), pp. e21-e21.

Gennequin Benjamin et al: "CRISPR/Cas-induced double-strand breaks boost the frequency of gene replacements for humanizing the mouseCnr2gene", Biochemical and Biophysical Research Communications, vol. 441, No. 4, Nov. 6, 2013 (Nov. 6, 2013), pp. 815-819.

P. Mali et al: "RNA-Guided Human Genome 1-13 Engineering via Cas9," Science, vol. 339, No. 6121, Feb. 15, 2013 (Feb. 15, 2013), pp. 823-826.

Gratz, Scott J. et al., "Genome Engineering of *Drosophila* with the CRISPR RNA-Guided Cas9 Nuclease". Genetics, vol. 194 (Aug. 2013), pp. 1029-1035 and Supporting Information.

Inbar, Ori et al., "The Relationship between Homology Length and Crossing Over during the Repair of a Broken Chromosome". The Journal of Biological Chemistry, vol. 275, No. 40 (2000), pp. 30833-30838.

Jinek, Martin et al., "A Programmable Dual-RNA-Guided DNA Endonuclease in Adaptive Bacterial Immunity". Science vol. 337 (Aug. 2012), pp. 816-821 and Supplementary Materials (document showing common technical knowledge).

Lan, Xiu-wan et al., "Influence of flanking sequence length on homologous recombination frequency in Cryphonectria parasitica". Journal of Guangxi Agricultural and Biological Science, vol. 26 (Jun. 2007), Sup., pp. 1-6.

Mali, Prashant et al., "RNA-Guided Human Genome Engineering via Cas9," Science, vol. 339 (Jan. 2013 (online)), pp. 823-826 and Supplementary Materials.

Moehle, Erica A. et al., "Targeted gene addition into a specified location in the human genome using designed zinc finger nucleases". Proceedings of the National Academy of Sciences of the USA, vol. 104, No. 9 (Feb. 27, 2007), pp. 3055-3060.

Jun. 1, 2020—Grounds of Opposition filed against EP 3,071,698.

Gratz et al., "CRISPR/Cas9-mediated genome engineering and the promise of designer flies on demand," Fly, vol. 7:4, pp. 249-255 (2013).

Beumer et al., "Donor DNA Utilization During Gene Targeting with Zinc-Finger Nucleases," Genes Genomes Genetics, vol. 3, pages 657-664 (2013) plus supplementary material.

Chen et al., "Efficient genome editing in Caenorhabditis elegans by CRISPR-targeted homologous recombination," Nucleic Acids Research, vol. 41, No. 20, e193, pp. 1-6 (2013) plus supplementary material.

Meyer et al., "Gene targeting by homologous recombination in mouse zygotes mediated by zinc-finger nucleases," PNAS, vol. 107, No. 34, pp. 15022-15026 (2010) plus supporting information.

Cong et al., "Multiplex Genome Engineering Using CRISPR/Cas Systems," Science, vol. 339, pp. 819-823 (2013) plus supplementary material.

Applicant's Letter of 15 Jun. 2018 to the Examining Division for EP App. No. 14864325.7 (granted as Patent No. EP 3,071,698).

Addgene Map of pHD-DsRed showing size of loxP-3xP3-DsRed-LoxP gene. Retrieved from URL https://www.addgene.org/51434 on May 19, 2020.

Addgene Map of pUASTP2 showing size of mini-white gene. Retrieved from URL https://addgene.org/13843 on May 15, 2020.

Jun. 19, 2020—Examination Report issued for EP 19194177.2.

\* cited by examiner

Figure 8
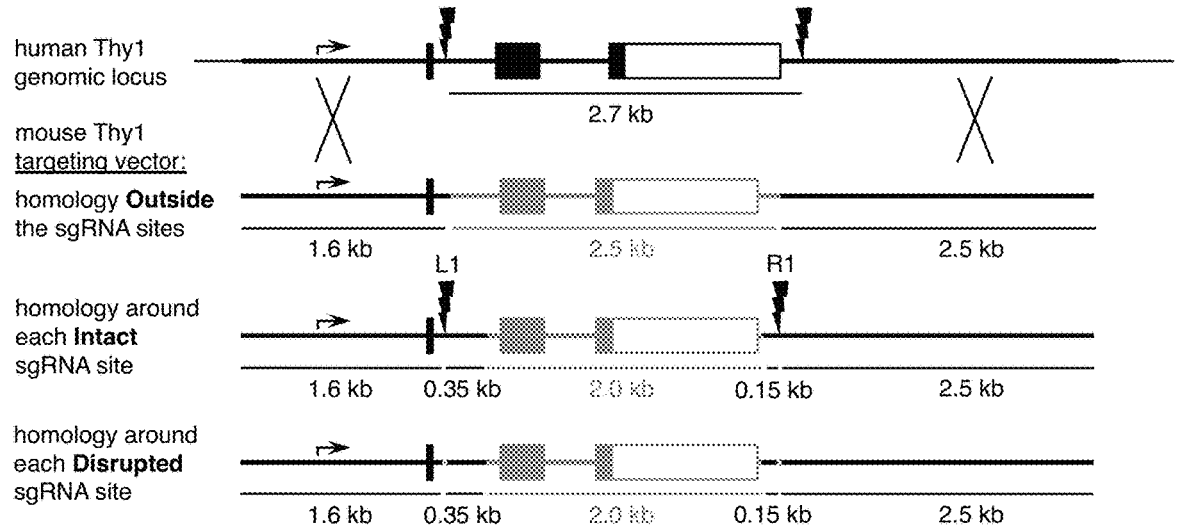
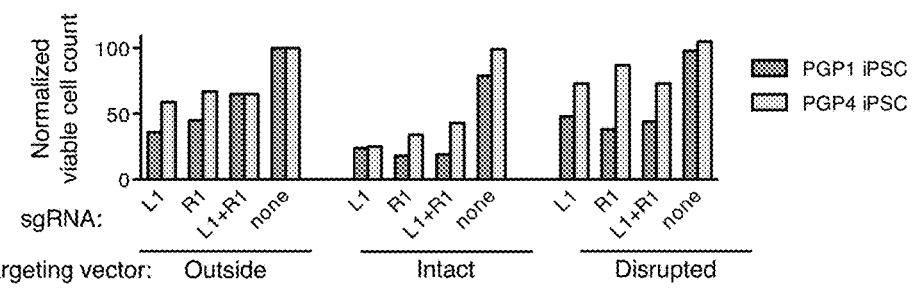
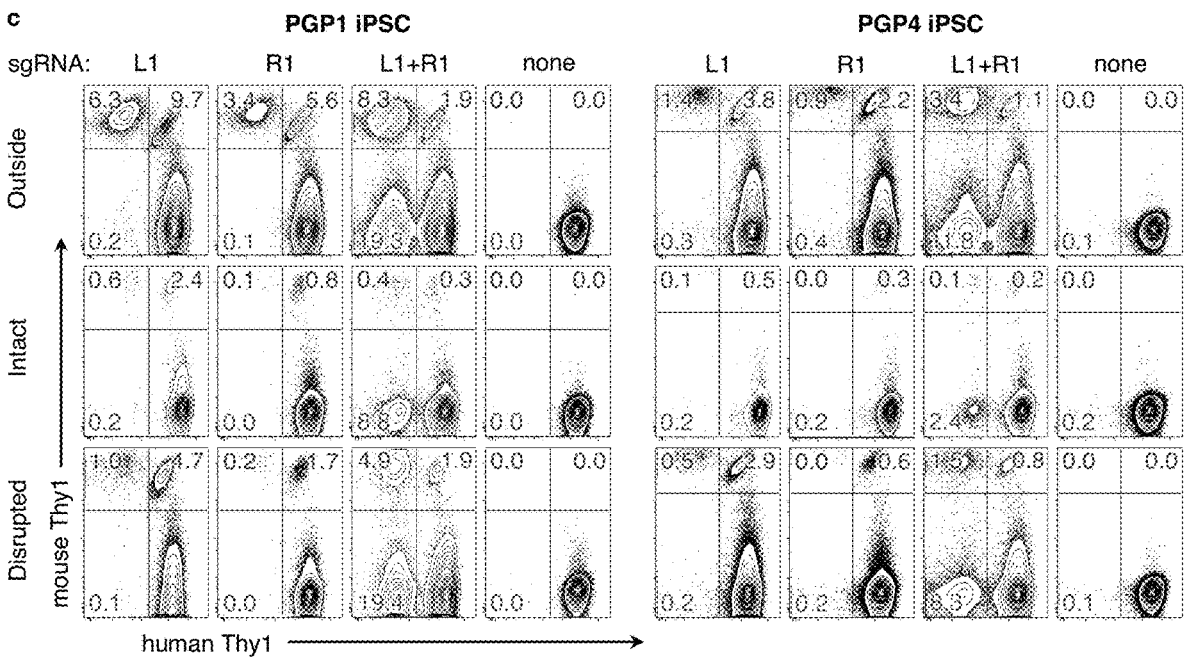

SEQUENCE LISTING

<160> NUMBER OF SEQ ID NOS: 120

<210> SEQ ID NO 1
<211> LENGTH: 1368
<212> TYPE: PRT
<213> ORGANISM: Streptococcus pyogenes

<400> SEQUENCE: 1

```
Met Asp Lys Lys Tyr Ser Ile Gly Leu Asp Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125

His Glu Lys Tyr Pro Thr Ile Tyr His Leu Arg Lys Lys Leu Val Asp
    130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
        195                 200                 205

Lys Ala Ile Leu Ser Ala Arg Leu Ser Lys Ser Arg Arg Leu Glu Asn
    210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
            260                 265                 270

Asp Asp Leu Asp Asn Leu Leu Ala Gln Ile Gly Asp Gln Tyr Ala Asp
        275                 280                 285

Leu Phe Leu Ala Ala Lys Asn Leu Ser Asp Ala Ile Leu Leu Ser Asp
    290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
            340                 345                 350

Asp Gln Ser Lys Asn Gly Tyr Ala Gly Tyr Ile Asp Gly Gly Ala Ser
        355                 360                 365
```

-continued

```
Gln Glu Glu Phe Tyr Lys Phe Ile Lys Pro Ile Leu Glu Lys Met Asp
    370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
                405                 410                 415

Gly Glu Leu His Ala Ile Leu Arg Arg Gln Glu Asp Phe Tyr Pro Phe
            420                 425                 430

Leu Lys Asp Asn Arg Glu Lys Ile Glu Lys Ile Leu Thr Phe Arg Ile
        435                 440                 445

Pro Tyr Tyr Val Gly Pro Leu Ala Arg Gly Asn Ser Arg Phe Ala Trp
    450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
                485                 490                 495

Asn Phe Asp Lys Asn Leu Pro Asn Glu Lys Val Leu Pro Lys His Ser
            500                 505                 510

Leu Leu Tyr Glu Tyr Phe Thr Val Tyr Asn Glu Leu Thr Lys Val Lys
        515                 520                 525

Tyr Val Thr Glu Gly Met Arg Lys Pro Ala Phe Leu Ser Gly Glu Gln
    530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
                565                 570                 575

Ser Val Glu Ile Ser Gly Val Glu Asp Arg Phe Asn Ala Ser Leu Gly
            580                 585                 590

Thr Tyr His Asp Leu Leu Lys Ile Ile Lys Asp Lys Asp Phe Leu Asp
        595                 600                 605

Asn Glu Glu Asn Glu Asp Ile Leu Glu Asp Ile Val Leu Thr Leu Thr
    610                 615                 620

Leu Phe Glu Asp Arg Glu Met Ile Glu Glu Arg Leu Lys Thr Tyr Ala
625                 630                 635                 640

His Leu Phe Asp Asp Lys Val Met Lys Gln Leu Lys Arg Arg Arg Tyr
                645                 650                 655

Thr Gly Trp Gly Arg Leu Ser Arg Lys Leu Ile Asn Gly Ile Arg Asp
            660                 665                 670

Lys Gln Ser Gly Lys Thr Ile Leu Asp Phe Leu Lys Ser Asp Gly Phe
        675                 680                 685

Ala Asn Arg Asn Phe Met Gln Leu Ile His Asp Asp Ser Leu Thr Phe
    690                 695                 700

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
                725                 730                 735

Ile Leu Gln Thr Val Lys Val Val Asp Glu Leu Val Lys Val Met Gly
            740                 745                 750

Arg His Lys Pro Glu Asn Ile Val Ile Glu Met Ala Arg Glu Asn Gln
        755                 760                 765

Thr Thr Gln Lys Gly Gln Lys Asn Ser Arg Glu Arg Met Lys Arg Ile
    770                 775                 780

Glu Glu Gly Ile Lys Glu Leu Gly Ser Gln Ile Leu Lys Glu His Pro
```

-continued

```
            785                 790                 795                 800
Val Glu Asn Thr Gln Leu Gln Asn Glu Lys Leu Tyr Leu Tyr Tyr Leu
                    805                 810                 815

Gln Asn Gly Arg Asp Met Tyr Val Asp Gln Glu Leu Asp Ile Asn Arg
                820                 825                 830

Leu Ser Asp Tyr Asp Val Asp His Ile Val Pro Gln Ser Phe Leu Lys
                835                 840                 845

Asp Asp Ser Ile Asp Asn Lys Val Leu Thr Arg Ser Asp Lys Asn Arg
850                 855                 860

Gly Lys Ser Asp Asn Val Pro Ser Glu Glu Val Val Lys Lys Met Lys
865                 870                 875                 880

Asn Tyr Trp Arg Gln Leu Leu Asn Ala Lys Leu Ile Thr Gln Arg Lys
                    885                 890                 895

Phe Asp Asn Leu Thr Lys Ala Glu Arg Gly Gly Leu Ser Glu Leu Asp
                900                 905                 910

Lys Ala Gly Phe Ile Lys Arg Gln Leu Val Glu Thr Arg Gln Ile Thr
                915                 920                 925

Lys His Val Ala Gln Ile Leu Asp Ser Arg Met Asn Thr Lys Tyr Asp
                930                 935                 940

Glu Asn Asp Lys Leu Ile Arg Glu Val Lys Val Ile Thr Leu Lys Ser
945                 950                 955                 960

Lys Leu Val Ser Asp Phe Arg Lys Asp Phe Gln Phe Tyr Lys Val Arg
                    965                 970                 975

Glu Ile Asn Asn Tyr His His Ala His Asp Ala Tyr Leu Asn Ala Val
                980                 985                 990

Val Gly Thr Ala Leu Ile Lys Lys  Tyr Pro Lys Leu Glu  Ser Glu Phe
                995                 1000                1005

Val Tyr  Gly Asp Tyr Lys Val  Tyr Asp Val Arg Lys  Met Ile Ala
        1010                1015                1020

Lys Ser  Glu Gln Glu Ile Gly  Lys Ala Thr Ala Lys  Tyr Phe Phe
        1025                1030                1035

Tyr Ser  Asn Ile Met Asn Phe  Phe Lys Thr Glu Ile  Thr Leu Ala
        1040                1045                1050

Asn Gly  Glu Ile Arg Lys Arg  Pro Leu Ile Glu Thr  Asn Gly Glu
        1055                1060                1065

Thr Gly  Glu Ile Val Trp Asp  Lys Gly Arg Asp Phe  Ala Thr Val
        1070                1075                1080

Arg Lys  Val Leu Ser Met Pro  Gln Val Asn Ile Val  Lys Lys Thr
        1085                1090                1095

Glu Val  Gln Thr Gly Gly Phe  Ser Lys Glu Ser Ile  Leu Pro Lys
        1100                1105                1110

Arg Asn  Ser Asp Lys Leu Ile  Ala Arg Lys Lys Asp  Trp Asp Pro
        1115                1120                1125

Lys Lys  Tyr Gly Gly Phe Asp  Ser Pro Thr Val Ala  Tyr Ser Val
        1130                1135                1140

Leu Val  Val Ala Lys Val Glu  Lys Gly Lys Ser Lys  Lys Leu Lys
        1145                1150                1155

Ser Val  Lys Glu Leu Leu Gly  Ile Thr Ile Met Glu  Arg Ser Ser
        1160                1165                1170

Phe Glu  Lys Asn Pro Ile Asp  Phe Leu Glu Ala Lys  Gly Tyr Lys
        1175                1180                1185

Glu Val  Lys Lys Asp Leu Ile  Ile Lys Leu Pro Lys  Tyr Ser Leu
        1190                1195                1200
```

Phe Glu Leu Glu Asn Gly Arg Lys Arg Met Leu Ala Ser Ala Gly
    1205                1210                1215

Glu Leu Gln Lys Gly Asn Glu Leu Ala Leu Pro Ser Lys Tyr Val
    1220                1225                1230

Asn Phe Leu Tyr Leu Ala Ser His Tyr Glu Lys Leu Lys Gly Ser
    1235                1240                1245

Pro Glu Asp Asn Glu Gln Lys Gln Leu Phe Val Glu Gln His Lys
    1250                1255                1260

His Tyr Leu Asp Glu Ile Ile Glu Gln Ile Ser Glu Phe Ser Lys
    1265                1270                1275

Arg Val Ile Leu Ala Asp Ala Asn Leu Asp Lys Val Leu Ser Ala
    1280                1285                1290

Tyr Asn Lys His Arg Asp Lys Pro Ile Arg Glu Gln Ala Glu Asn
    1295                1300                1305

Ile Ile His Leu Phe Thr Leu Thr Asn Leu Gly Ala Pro Ala Ala
    1310                1315                1320

Phe Lys Tyr Phe Asp Thr Thr Ile Asp Arg Lys Arg Tyr Thr Ser
    1325                1330                1335

Thr Lys Glu Val Leu Asp Ala Thr Leu Ile His Gln Ser Ile Thr
    1340                1345                1350

Gly Leu Tyr Glu Thr Arg Ile Asp Leu Ser Gln Leu Gly Gly Asp
    1355                1360                1365

<210> SEQ ID NO 2
<211> LENGTH: 22
<212> TYPE: DNA
<213> ORGANISM: Artificial
<220> FEATURE:
<223> OTHER INFORMATION: Target oligonucleotide

<400> SEQUENCE: 2
cacagtctca gaaaagcgca gg                                              22

<210> SEQ ID NO 3
<211> LENGTH: 22
<212> TYPE: DNA
<213> ORGANISM: Artificial
<220> FEATURE:
<223> OTHER INFORMATION: Target oligonucleotide

<400> SEQUENCE: 3
aaatatcagc gcggtggatt gg                                              22

<210> SEQ ID NO 4
<211> LENGTH: 22
<212> TYPE: DNA
<213> ORGANISM: Artificial
<220> FEATURE:
<223> OTHER INFORMATION: Target oligonucleotide

<400> SEQUENCE: 4
ggtcaggctg aactcgtact gg                                              22

<210> SEQ ID NO 5
<211> LENGTH: 22
<212> TYPE: DNA
<213> ORGANISM: Artificial
<220> FEATURE:
<223> OTHER INFORMATION: Target oligonucleotide

<400> SEQUENCE: 5
ttagtagcaa cgctacccca gg    22

<210> SEQ ID NO 6
<211> LENGTH: 22
<212> TYPE: DNA
<213> ORGANISM: Artificial
<220> FEATURE:
<223> OTHER INFORMATION: Target oligonucleotide

<400> SEQUENCE: 6
gtgtgcagtc attagcccct gg    22

<210> SEQ ID NO 7
<211> LENGTH: 22
<212> TYPE: DNA
<213> ORGANISM: Artificial
<220> FEATURE:
<223> OTHER INFORMATION: Target oligonucleotide

<400> SEQUENCE: 7
gggcaaatgt gtctcgttag gg    22

<210> SEQ ID NO 8
<211> LENGTH: 22
<212> TYPE: DNA
<213> ORGANISM: Artificial
<220> FEATURE:
<223> OTHER INFORMATION: Target oligonucleotide

<400> SEQUENCE: 8
ttctcctttc cgaagtccgt gg    22

<210> SEQ ID NO 9
<211> LENGTH: 22
<212> TYPE: DNA
<213> ORGANISM: Artificial
<220> FEATURE:
<223> OTHER INFORMATION: Target oligonucleotide

<400> SEQUENCE: 9
gccgctgtcg cctggcaaaa gg    22

<210> SEQ ID NO 10
<211> LENGTH: 22
<212> TYPE: DNA
<213> ORGANISM: Artificial
<220> FEATURE:
<223> OTHER INFORMATION: Target oligonucleotide

<400> SEQUENCE: 10
gatggtagac atcgaccatg gg    22

<210> SEQ ID NO 11
<211> LENGTH: 22
<212> TYPE: DNA
<213> ORGANISM: Artificial
<220> FEATURE:
<223> OTHER INFORMATION: Target oligonucleotide

<400> SEQUENCE: 11
ttcaatttcg ggcccgatct gg    22

<210> SEQ ID NO 12
<211> LENGTH: 22
<212> TYPE: DNA

```
<213> ORGANISM: Artificial
<220> FEATURE:
<223> OTHER INFORMATION: Target oligonucleotide

<400> SEQUENCE: 12
tgagtcgcgt cacggctatt gg                                              22

<210> SEQ ID NO 13
<211> LENGTH: 22
<212> TYPE: DNA
<213> ORGANISM: Artificial
<220> FEATURE:
<223> OTHER INFORMATION: Target oligonucleotide

<400> SEQUENCE: 13
catttgcggt ggtaatcgca gg                                              22

<210> SEQ ID NO 14
<211> LENGTH: 22
<212> TYPE: DNA
<213> ORGANISM: Artificial
<220> FEATURE:
<223> OTHER INFORMATION: Target oligonucleotide

<400> SEQUENCE: 14
gatcggatcg ggtcgcgtcg gg                                              22

<210> SEQ ID NO 15
<211> LENGTH: 22
<212> TYPE: DNA
<213> ORGANISM: Artificial
<220> FEATURE:
<223> OTHER INFORMATION: Target oligonucleotide

<400> SEQUENCE: 15
tttcctgcgc tgaatcgggt gg                                              22

<210> SEQ ID NO 16
<211> LENGTH: 22
<212> TYPE: DNA
<213> ORGANISM: Artificial
<220> FEATURE:
<223> OTHER INFORMATION: Target oligonucleotide

<400> SEQUENCE: 16
ggctcctgtc tgtgcctgac gg                                              22

<210> SEQ ID NO 17
<211> LENGTH: 47
<212> TYPE: DNA
<213> ORGANISM: Artificial
<220> FEATURE:
<223> OTHER INFORMATION: PCR primer

<400> SEQUENCE: 17
ctttcttgta caaagttggc attattagac gtcaggtggc actttc                    47

<210> SEQ ID NO 18
<211> LENGTH: 47
<212> TYPE: DNA
<213> ORGANISM: Artificial
<220> FEATURE:
<223> OTHER INFORMATION: PCR primer

<400> SEQUENCE: 18
cctttaaagc ctgcttttttt gtacagtttg cgtattgggc gctcttc                  47
```

<210> SEQ ID NO 19
<211> LENGTH: 24
<212> TYPE: DNA
<213> ORGANISM: Artificial
<220> FEATURE:
<223> OTHER INFORMATION: PCR primer

<400> SEQUENCE: 19
gccaccatgg acaagaagta ctcc                                      24

<210> SEQ ID NO 20
<211> LENGTH: 24
<212> TYPE: DNA
<213> ORGANISM: Artificial
<220> FEATURE:
<223> OTHER INFORMATION: PCR primer

<400> SEQUENCE: 20
tcacaccttc ctcttcttct tggg                                      24

<210> SEQ ID NO 21
<211> LENGTH: 48
<212> TYPE: DNA
<213> ORGANISM: Artificial
<220> FEATURE:
<223> OTHER INFORMATION: PCR primer

<400> SEQUENCE: 21
ccgaaaagtg ccacctgacg tcgacggatg aaaggagtgg gaattggc             48

<210> SEQ ID NO 22
<211> LENGTH: 50
<212> TYPE: DNA
<213> ORGANISM: Artificial
<220> FEATURE:
<223> OTHER INFORMATION: PCR primer

<400> SEQUENCE: 22
ggagtacttc ttgtccatgg tggcggccaa ctagccagct tgggtctccc           50

<210> SEQ ID NO 23
<211> LENGTH: 54
<212> TYPE: DNA
<213> ORGANISM: Artificial
<220> FEATURE:
<223> OTHER INFORMATION: PCR primer

<400> SEQUENCE: 23
gctgacccca agaagaagag gaaggtgtga catcaccatt gagtttaaac ccgc      54

<210> SEQ ID NO 24
<211> LENGTH: 45
<212> TYPE: DNA
<213> ORGANISM: Artificial
<220> FEATURE:
<223> OTHER INFORMATION: PCR primer

<400> SEQUENCE: 24
ccaagctcta gctagaggtc gacggtatcg agccccagct ggttc                45

<210> SEQ ID NO 25
<211> LENGTH: 21
<212> TYPE: DNA
<213> ORGANISM: Artificial
<220> FEATURE:

<223> OTHER INFORMATION: PCR primer

<400> SEQUENCE: 25
ataccgtcga cctctagcta g                                              21

<210> SEQ ID NO 26
<211> LENGTH: 18
<212> TYPE: DNA
<213> ORGANISM: Artificial
<220> FEATURE:
<223> OTHER INFORMATION: PCR primer

<400> SEQUENCE: 26
tccgtcgacg tcaggtgg                                                  18

<210> SEQ ID NO 27
<211> LENGTH: 23
<212> TYPE: DNA
<213> ORGANISM: Artificial
<220> FEATURE:
<223> OTHER INFORMATION: PCR primer

<400> SEQUENCE: 27
tggtggtggt tgtggtacac acc                                            23

<210> SEQ ID NO 28
<211> LENGTH: 21
<212> TYPE: DNA
<213> ORGANISM: Artificial
<220> FEATURE:
<223> OTHER INFORMATION: PCR primer

<400> SEQUENCE: 28
aatagggagg gccggggtac c                                              21

<210> SEQ ID NO 29
<211> LENGTH: 26
<212> TYPE: DNA
<213> ORGANISM: Artificial
<220> FEATURE:
<223> OTHER INFORMATION: PCR primer

<400> SEQUENCE: 29
acccttcccc tcctagatcc caagcc                                         26

<210> SEQ ID NO 30
<211> LENGTH: 52
<212> TYPE: DNA
<213> ORGANISM: Artificial
<220> FEATURE:
<223> OTHER INFORMATION: PCR primer

<400> SEQUENCE: 30
gattaaaggt gtgtaccaca accaccacca cttttctgag actgtgaggg ag            52

<210> SEQ ID NO 31
<211> LENGTH: 49
<212> TYPE: DNA
<213> ORGANISM: Artificial
<220> FEATURE:
<223> OTHER INFORMATION: PCR primer

<400> SEQUENCE: 31
agactctggg gtaccccggc cctccctatt cccagggget aatgactgc                49

```
<210> SEQ ID NO 32
<211> LENGTH: 20
<212> TYPE: DNA
<213> ORGANISM: Artificial
<220> FEATURE:
<223> OTHER INFORMATION: PCR primer

<400> SEQUENCE: 32
gcacctccag ccatcacagc                                               20

<210> SEQ ID NO 33
<211> LENGTH: 53
<212> TYPE: DNA
<213> ORGANISM: Artificial
<220> FEATURE:
<223> OTHER INFORMATION: PCR primer

<400> SEQUENCE: 33
ccaggaaggg gctgtgatgg ctggaggtgc ttagacgtca ggtggcactt ttc           53

<210> SEQ ID NO 34
<211> LENGTH: 47
<212> TYPE: DNA
<213> ORGANISM: Artificial
<220> FEATURE:
<223> OTHER INFORMATION: PCR primer

<400> SEQUENCE: 34
gggcttggga tctaggaggg gaagggtttg cgtattgggc gctcttc                 47

<210> SEQ ID NO 35
<211> LENGTH: 26
<212> TYPE: DNA
<213> ORGANISM: Artificial
<220> FEATURE:
<223> OTHER INFORMATION: PCR primer

<400> SEQUENCE: 35
acccttcccc tcctagatcc caagcc                                        26

<210> SEQ ID NO 36
<211> LENGTH: 20
<212> TYPE: DNA
<213> ORGANISM: Artificial
<220> FEATURE:
<223> OTHER INFORMATION: PCR primer

<400> SEQUENCE: 36
gcacctccag ccatcacagc                                               20

<210> SEQ ID NO 37
<211> LENGTH: 26
<212> TYPE: DNA
<213> ORGANISM: Artificial
<220> FEATURE:
<223> OTHER INFORMATION: PCR primer

<400> SEQUENCE: 37
acccttcccc tcctagatcc caagcc                                        26

<210> SEQ ID NO 38
<211> LENGTH: 33
<212> TYPE: DNA
<213> ORGANISM: Artificial
<220> FEATURE:
<223> OTHER INFORMATION: PCR primer
```

<400> SEQUENCE: 38
aagattcaga gagattcatt cattcattca caa                          33

<210> SEQ ID NO 39
<211> LENGTH: 23
<212> TYPE: DNA
<213> ORGANISM: Artificial
<220> FEATURE:
<223> OTHER INFORMATION: PCR primer

<400> SEQUENCE: 39
cctgctaaca ggtacccggc atg                                     23

<210> SEQ ID NO 40
<211> LENGTH: 20
<212> TYPE: DNA
<213> ORGANISM: Artificial
<220> FEATURE:
<223> OTHER INFORMATION: PCR primer

<400> SEQUENCE: 40
gcacctccag ccatcacagc                                         20

<210> SEQ ID NO 41
<211> LENGTH: 25
<212> TYPE: DNA
<213> ORGANISM: Artificial
<220> FEATURE:
<223> OTHER INFORMATION: PCR primer

<400> SEQUENCE: 41
cagcatcttg ctaaggggtt gtcag                                   25

<210> SEQ ID NO 42
<211> LENGTH: 25
<212> TYPE: DNA
<213> ORGANISM: Artificial
<220> FEATURE:
<223> OTHER INFORMATION: PCR primer

<400> SEQUENCE: 42
gtcagcagac atgggatgtt cgttt                                   25

<210> SEQ ID NO 43
<211> LENGTH: 47
<212> TYPE: DNA
<213> ORGANISM: Artificial
<220> FEATURE:
<223> OTHER INFORMATION: PCR primer

<400> SEQUENCE: 43
gggcttggga tctaggaggg gaagggtttg cgtattgggc gctcttc            47

<210> SEQ ID NO 44
<211> LENGTH: 52
<212> TYPE: DNA
<213> ORGANISM: Artificial
<220> FEATURE:
<223> OTHER INFORMATION: PCR primer

<400> SEQUENCE: 44
tgaatgaatg aatgaatctc tctgaatctt gtttgcgtat tgggcgctct tc      52

<210> SEQ ID NO 45
<211> LENGTH: 52

```
<212> TYPE: DNA
<213> ORGANISM: Artificial
<220> FEATURE:
<223> OTHER INFORMATION: PCR primer

<400> SEQUENCE: 45
tcctgcccca tgccgggtac ctgttagcag gtttgcgtat tgggcgctct tc          52

<210> SEQ ID NO 46
<211> LENGTH: 53
<212> TYPE: DNA
<213> ORGANISM: Artificial
<220> FEATURE:
<223> OTHER INFORMATION: PCR primer

<400> SEQUENCE: 46
ccaggaaggg gctgtgatgg ctggaggtgc ttagacgtca ggtggcactt ttc         53

<210> SEQ ID NO 47
<211> LENGTH: 53
<212> TYPE: DNA
<213> ORGANISM: Artificial
<220> FEATURE:
<223> OTHER INFORMATION: PCR primer

<400> SEQUENCE: 47
ggaggctgac aaccccttag caagatgctg ttagacgtca ggtggcactt ttc         53

<210> SEQ ID NO 48
<211> LENGTH: 53
<212> TYPE: DNA
<213> ORGANISM: Artificial
<220> FEATURE:
<223> OTHER INFORMATION: PCR primer

<400> SEQUENCE: 48
caaataaacg aacatcccat gtctgctgac ttagacgtca ggtggcactt ttc         53

<210> SEQ ID NO 49
<211> LENGTH: 24
<212> TYPE: DNA
<213> ORGANISM: Artificial
<220> FEATURE:
<223> OTHER INFORMATION: PCR primer

<400> SEQUENCE: 49
ccttcccctc ctagatccca agcc                                         24

<210> SEQ ID NO 50
<211> LENGTH: 20
<212> TYPE: DNA
<213> ORGANISM: Artificial
<220> FEATURE:
<223> OTHER INFORMATION: PCR primer

<400> SEQUENCE: 50
gcacctccag ccatcacagc                                              20

<210> SEQ ID NO 51
<211> LENGTH: 23
<212> TYPE: DNA
<213> ORGANISM: Artificial
<220> FEATURE:
<223> OTHER INFORMATION: PCR primer

<400> SEQUENCE: 51
```
tcttgtttga gatgttgtgc ggg                                                      23

<210> SEQ ID NO 52
<211> LENGTH: 25
<212> TYPE: DNA
<213> ORGANISM: Artificial
<220> FEATURE:
<223> OTHER INFORMATION: PCR primer

<400> SEQUENCE: 52
ctggtttcag cactccgatc ctatc                                                    25

<210> SEQ ID NO 53
<211> LENGTH: 20
<212> TYPE: DNA
<213> ORGANISM: Artificial
<220> FEATURE:
<223> OTHER INFORMATION: PCR primer

<400> SEQUENCE: 53
tgtggctctg caccaggaag                                                          20

<210> SEQ ID NO 54
<211> LENGTH: 23
<212> TYPE: DNA
<213> ORGANISM: Artificial
<220> FEATURE:
<223> OTHER INFORMATION: PCR primer

<400> SEQUENCE: 54 cctctcccett ttccctggtt ttg                                                     23

<210> SEQ ID NO 55
<211> LENGTH: 53
<212> TYPE: DNA
<213> ORGANISM: Artificial
<220> FEATURE:
<223> OTHER INFORMATION: PCR primer

<400> SEQUENCE: 55
tactctgcaa aaccagggaa aagggagagg ttagacgtca ggtggcactt ttc                     53

<210> SEQ ID NO 56
<211> LENGTH: 52
<212> TYPE: DNA
<213> ORGANISM: Artificial
<220> FEATURE:
<223> OTHER INFORMATION: PCR primer

<400> SEQUENCE: 56
ctgtggatag gatcggagtg ctgaaaccag gtttgcgtat tgggcgctct tc                      52

<210> SEQ ID NO 57
<211> LENGTH: 54
<212> TYPE: DNA
<213> ORGANISM: Artificial
<220> FEATURE:
<223> OTHER INFORMATION: PCR primer

<400> SEQUENCE: 57
atctctccac ttcaggtggg tgggaggccc ctgtggtctg tgtctcccca aatt                    54

<210> SEQ ID NO 58
<211> LENGTH: 56
<212> TYPE: DNA
<213> ORGANISM: Artificial

```
<220> FEATURE:
<223> OTHER INFORMATION: PCR primer

<400> SEQUENCE: 58
caggtggaca ggaggacaga ttccagaggc ttggttttat tgtgcagttt tctttc          56

<210> SEQ ID NO 59
<211> LENGTH: 19
<212> TYPE: DNA
<213> ORGANISM: Artificial
<220> FEATURE:
<223> OTHER INFORMATION: PCR primer

<400> SEQUENCE: 59
ggcttccttc cctccagag                                                   19

<210> SEQ ID NO 60
<211> LENGTH: 17
<212> TYPE: DNA
<213> ORGANISM: Artificial
<220> FEATURE:
<223> OTHER INFORMATION: PCR primer

<400> SEQUENCE: 60
acaggggcct cccaccc                                                     17

<210> SEQ ID NO 61
<211> LENGTH: 22
<212> TYPE: DNA
<213> ORGANISM: Artificial
<220> FEATURE:
<223> OTHER INFORMATION: PCR primer

<400> SEQUENCE: 61
caagcctctg gaatctgtcc tc                                               22

<210> SEQ ID NO 62
<211> LENGTH: 21
<212> TYPE: DNA
<213> ORGANISM: Artificial
<220> FEATURE:
<223> OTHER INFORMATION: PCR primer

<400> SEQUENCE: 62
gcccagtgtg cagtcattag c                                                21

<210> SEQ ID NO 63
<211> LENGTH: 22
<212> TYPE: DNA
<213> ORGANISM: Artificial
<220> FEATURE:
<223> OTHER INFORMATION: PCR primer

<400> SEQUENCE: 63
cttttctgag actgtgaggg ag                                               22

<210> SEQ ID NO 64
<211> LENGTH: 24
<212> TYPE: DNA
<213> ORGANISM: Artificial
<220> FEATURE:
<223> OTHER INFORMATION: PCR primer

<400> SEQUENCE: 64
taccccaggg gctaatgact gcac                                             24
```

<210> SEQ ID NO 65
<211> LENGTH: 28
<212> TYPE: DNA
<213> ORGANISM: Artificial
<220> FEATURE:
<223> OTHER INFORMATION: PCR primer

<400> SEQUENCE: 65
acagtctcag aaaacgcagg tgacaaag                                    28

<210> SEQ ID NO 66
<211> LENGTH: 30
<212> TYPE: DNA
<213> ORGANISM: Artificial
<220> FEATURE:
<223> OTHER INFORMATION: PCR primer

<400> SEQUENCE: 66
cattagcccc tgggtagcgt tgctactaag                                  30

<210> SEQ ID NO 67
<211> LENGTH: 29
<212> TYPE: DNA
<213> ORGANISM: Artificial
<220> FEATURE:
<223> OTHER INFORMATION: PCR primer

<400> SEQUENCE: 67
ttgtcacctg cgttttctga gactgtgag                                   29

<210> SEQ ID NO 68
<211> LENGTH: 30
<212> TYPE: DNA
<213> ORGANISM: Artificial
<220> FEATURE:
<223> OTHER INFORMATION: PCR primer

<400> SEQUENCE: 68
cttagtagca acgctaccca ggggctaatg                                  30

<210> SEQ ID NO 69
<211> LENGTH: 52
<212> TYPE: DNA
<213> ORGANISM: Artificial
<220> FEATURE:
<223> OTHER INFORMATION: PCR primer

<400> SEQUENCE: 69
gagaatacca gcagttcacc catccagtac gaaattctac cgggtagggg ag         52

<210> SEQ ID NO 70
<211> LENGTH: 54
<212> TYPE: DNA
<213> ORGANISM: Artificial
<220> FEATURE:
<223> OTHER INFORMATION: PCR primer

<400> SEQUENCE: 70
cccagtgtgc agtcattagc ccctggggta cgacggccag tgaattgtaa tacg       54

<210> SEQ ID NO 71
<211> LENGTH: 26
<212> TYPE: DNA
<213> ORGANISM: Artificial
<220> FEATURE:
<223> OTHER INFORMATION: PCR primer

```
<400> SEQUENCE: 71
acccttcccc tcctagatcc caagcc                                       26

<210> SEQ ID NO 72
<211> LENGTH: 28
<212> TYPE: DNA
<213> ORGANISM: Artificial
<220> FEATURE:
<223> OTHER INFORMATION: PCR primer

<400> SEQUENCE: 72
gtactggatg ggtgaactgc tggtattc                                     28

<210> SEQ ID NO 73
<211> LENGTH: 24
<212> TYPE: DNA
<213> ORGANISM: Artificial
<220> FEATURE:
<223> OTHER INFORMATION: PCR primer

<400> SEQUENCE: 73
taccccaggg gctaatgact gcac                                         24

<210> SEQ ID NO 74
<211> LENGTH: 20
<212> TYPE: DNA
<213> ORGANISM: Artificial
<220> FEATURE:
<223> OTHER INFORMATION: PCR primer

<400> SEQUENCE: 74
gcacctccag ccatcacagc                                              20

<210> SEQ ID NO 75
<211> LENGTH: 53
<212> TYPE: DNA
<213> ORGANISM: Artificial
<220> FEATURE:
<223> OTHER INFORMATION: PCR primer

<400> SEQUENCE: 75
ccaggaaggg gctgtgatgg ctggaggtgc ttagacgtca ggtggcactt ttc         53

<210> SEQ ID NO 76
<211> LENGTH: 47
<212> TYPE: DNA
<213> ORGANISM: Artificial
<220> FEATURE:
<223> OTHER INFORMATION: PCR primer

<400> SEQUENCE: 76
gggcttggga tctaggaggg gaagggtttg cgtattgggc gctcttc                47

<210> SEQ ID NO 77
<211> LENGTH: 69
<212> TYPE: DNA
<213> ORGANISM: Artificial
<220> FEATURE:
<223> OTHER INFORMATION: PCR primer

<400> SEQUENCE: 77
gaagtcgagg ttccaaggtc acagtgaggg ggccctggcc acccttgca ggttctccat   60 agtccacag                                                          69
```

<210> SEQ ID NO 78
<211> LENGTH: 25
<212> TYPE: DNA
<213> ORGANISM: Artificial
<220> FEATURE:
<223> OTHER INFORMATION: PCR primer

<400> SEQUENCE: 78
caacaacccc tcctgtatat gacct                                             25

<210> SEQ ID NO 79
<211> LENGTH: 25
<212> TYPE: DNA
<213> ORGANISM: Artificial
<220> FEATURE:
<223> OTHER INFORMATION: PCR primer

<400> SEQUENCE: 79
acacactttc aacctccaag agacg                                             25

<210> SEQ ID NO 80
<211> LENGTH: 23
<212> TYPE: DNA
<213> ORGANISM: Artificial
<220> FEATURE:
<223> OTHER INFORMATION: PCR primer

<400> SEQUENCE: 80
ctcactgtga ccttggaacc tcg                                               23

<210> SEQ ID NO 81
<211> LENGTH: 51
<212> TYPE: DNA
<213> ORGANISM: Artificial
<220> FEATURE:
<223> OTHER INFORMATION: PCR primer

<400> SEQUENCE: 81
tgttgaggtc atatacagga ggggttgttg cctgacgggg ttgggttttc c                51

<210> SEQ ID NO 82
<211> LENGTH: 23
<212> TYPE: DNA
<213> ORGANISM: Artificial
<220> FEATURE:
<223> OTHER INFORMATION: PCR primer

<400> SEQUENCE: 82
aagggagccc tgaggccttt tcc                                               23

<210> SEQ ID NO 83
<211> LENGTH: 47
<212> TYPE: DNA
<213> ORGANISM: Artificial
<220> FEATURE:
<223> OTHER INFORMATION: PCR primer

<400> SEQUENCE: 83
tcaggaaaag gcctcagggc tcccttagac gtcaggtggc acttttc                     47

<210> SEQ ID NO 84
<211> LENGTH: 47
<212> TYPE: DNA
<213> ORGANISM: Artificial
<220> FEATURE:
<223> OTHER INFORMATION: PCR primer

<400> SEQUENCE: 84
cgtctcttgg aggttgaaag tgtgtgtttg cgtattgggc gctcttc                47

<210> SEQ ID NO 85
<211> LENGTH: 18
<212> TYPE: DNA
<213> ORGANISM: Artificial
<220> FEATURE:
<223> OTHER INFORMATION: PCR primer

<400> SEQUENCE: 85
taccagcagt tcacccat                                                18

<210> SEQ ID NO 86
<211> LENGTH: 18
<212> TYPE: DNA
<213> ORGANISM: Artificial
<220> FEATURE:
<223> OTHER INFORMATION: PCR primer

<400> SEQUENCE: 86
tctttgtctc acgggtca                                                18

<210> SEQ ID NO 87
<211> LENGTH: 18
<212> TYPE: DNA
<213> ORGANISM: Artificial
<220> FEATURE:
<223> OTHER INFORMATION: PCR primer

<400> SEQUENCE: 87
tctccccaac cacttagt                                                18

<210> SEQ ID NO 88
<211> LENGTH: 18
<212> TYPE: DNA
<213> ORGANISM: Artificial
<220> FEATURE:
<223> OTHER INFORMATION: PCR primer

<400> SEQUENCE: 88
tgtgcagtca ttagcccc                                                18

<210> SEQ ID NO 89
<211> LENGTH: 25
<212> TYPE: DNA
<213> ORGANISM: Artificial
<220> FEATURE:
<223> OTHER INFORMATION: PCR primer

<400> SEQUENCE: 89
ggccgccacc atggattata aggac                                        25

<210> SEQ ID NO 90
<211> LENGTH: 20
<212> TYPE: DNA
<213> ORGANISM: Artificial
<220> FEATURE:
<223> OTHER INFORMATION: PCR primer

<400> SEQUENCE: 90
ggaacctgcc actcgatgtg                                              20

<210> SEQ ID NO 91

```
<211> LENGTH: 44
<212> TYPE: DNA
<213> ORGANISM: Artificial
<220> FEATURE:
<223> OTHER INFORMATION: PCR primer

<400> SEQUENCE: 91
gacatcacat cgagtggcag gttcccagct ggtgaagtcc gagc                    44

<210> SEQ ID NO 92
<211> LENGTH: 63
<212> TYPE: DNA
<213> ORGANISM: Artificial
<220> FEATURE:
<223> OTHER INFORMATION: PCR primer

<400> SEQUENCE: 92
caactagaag gcacagtcga ggctgatcag cggggttaga aattgatttc accattgttg    60
aac                                                                 63

<210> SEQ ID NO 93
<211> LENGTH: 50
<212> TYPE: DNA
<213> ORGANISM: Artificial
<220> FEATURE:
<223> OTHER INFORMATION: PCR primer

<400> SEQUENCE: 93
gacatcacat cgagtggcag gttcccaact agtcaaaagt gaactggagg              50

<210> SEQ ID NO 94
<211> LENGTH: 54
<212> TYPE: DNA
<213> ORGANISM: Artificial
<220> FEATURE:
<223> OTHER INFORMATION: PCR primer

<400> SEQUENCE: 94
caactagaag gcacagtcga ggctgatcag cgcccttaaa agtttatctc gccg          54

<210> SEQ ID NO 95
<211> LENGTH: 23
<212> TYPE: DNA
<213> ORGANISM: Artificial
<220> FEATURE:
<223> OTHER INFORMATION: PCR primer

<400> SEQUENCE: 95
gcctcgactg tgccttctag ttg                                           23

<210> SEQ ID NO 96
<211> LENGTH: 22
<212> TYPE: DNA
<213> ORGANISM: Artificial
<220> FEATURE:
<223> OTHER INFORMATION: PCR primer

<400> SEQUENCE: 96
cttataatcc atggtggcgg cc                                            22

<210> SEQ ID NO 97
<211> LENGTH: 25
<212> TYPE: DNA
<213> ORGANISM: Artificial
<220> FEATURE:
<223> OTHER INFORMATION: PCR primer
```

```
<400> SEQUENCE: 97
agggacttag atgactgcca tagcc                                              25

<210> SEQ ID NO 98
<211> LENGTH: 25
<212> TYPE: DNA
<213> ORGANISM: Artificial
<220> FEATURE:
<223> OTHER INFORMATION: PCR primer

<400> SEQUENCE: 98
atgttggcag taagcatgtt gttcc                                              25

<210> SEQ ID NO 99
<211> LENGTH: 25
<212> TYPE: DNA
<213> ORGANISM: Artificial
<220> FEATURE:
<223> OTHER INFORMATION: PCR primer

<400> SEQUENCE: 99
agggacttag atgactgcca tagcc                                              25

<210> SEQ ID NO 100
<211> LENGTH: 25
<212> TYPE: DNA
<213> ORGANISM: Artificial
<220> FEATURE:
<223> OTHER INFORMATION: PCR primer

<400> SEQUENCE: 100
ctcacctctg agcactgtga cgttc                                              25

<210> SEQ ID NO 101
<211> LENGTH: 25
<212> TYPE: DNA
<213> ORGANISM: Artificial
<220> FEATURE:
<223> OTHER INFORMATION: PCR primer

<400> SEQUENCE: 101
actgaagttc tgggtcccaa caatg                                              25

<210> SEQ ID NO 102
<211> LENGTH: 25
<212> TYPE: DNA
<213> ORGANISM: Artificial
<220> FEATURE:
<223> OTHER INFORMATION: PCR primer

<400> SEQUENCE: 102
atgaatacag actgcacctc cccag                                              25

<210> SEQ ID NO 103
<211> LENGTH: 25
<212> TYPE: DNA
<213> ORGANISM: Artificial
<220> FEATURE:
<223> OTHER INFORMATION: PCR primer

<400> SEQUENCE: 103
ctcacctctg agcactgtga cgttc                                              25

<210> SEQ ID NO 104
```

```
<211> LENGTH: 35
<212> TYPE: DNA
<213> ORGANISM: Artificial
<220> FEATURE:
<223> OTHER INFORMATION: PCR primer

<400> SEQUENCE: 104
ccatcaatct actgaagttc tgggtcccaa caatg                              35

<210> SEQ ID NO 105
<211> LENGTH: 25
<212> TYPE: DNA
<213> ORGANISM: Artificial
<220> FEATURE:
<223> OTHER INFORMATION: PCR primer

<400> SEQUENCE: 105
tgaagtgaaa ccctaaaggg ggaag                                         25

<210> SEQ ID NO 106
<211> LENGTH: 25
<212> TYPE: DNA
<213> ORGANISM: Artificial
<220> FEATURE:
<223> OTHER INFORMATION: PCR primer

<400> SEQUENCE: 106
aaaccacaca cttcaacctg gatgg                                         25

<210> SEQ ID NO 107
<211> LENGTH: 25
<212> TYPE: DNA
<213> ORGANISM: Artificial
<220> FEATURE:
<223> OTHER INFORMATION: PCR primer

<400> SEQUENCE: 107
gtttggccca agtttctaag ggagg                                         25

<210> SEQ ID NO 108
<211> LENGTH: 70
<212> TYPE: DNA
<213> ORGANISM: Artificial
<220> FEATURE:
<223> OTHER INFORMATION: PCR primer

<400> SEQUENCE: 108
tccctcacag tctcagaaaa gcgcaggtga taaccactta gtagcaacgc taccccaggg   60
gctaatgact                                                          70

<210> SEQ ID NO 109
<211> LENGTH: 38
<212> TYPE: DNA
<213> ORGANISM: Artificial
<220> FEATURE:
<223> OTHER INFORMATION: PCR primer

<400> SEQUENCE: 109
tccctcacag tctcagaaaa gcccaggggc taatgact                           38

<210> SEQ ID NO 110
<211> LENGTH: 23
<212> TYPE: DNA
<213> ORGANISM: Artificial
<220> FEATURE:
<223> OTHER INFORMATION: PCR primer
```

```
<400> SEQUENCE: 110
tccctcacag tctcagaatg act                                              23

<210> SEQ ID NO 111
<211> LENGTH: 38
<212> TYPE: DNA
<213> ORGANISM: Artificial
<220> FEATURE:
<223> OTHER INFORMATION: PCR primer

<400> SEQUENCE: 111
tccctcacag tctcagaaaa gcccaggggc taatgact                              38

<210> SEQ ID NO 112
<211> LENGTH: 42
<212> TYPE: DNA
<213> ORGANISM: Artificial
<220> FEATURE:
<223> OTHER INFORMATION: PCR primer

<400> SEQUENCE: 112
tccctcacag tctcagaact ttatcaccag gggctaatga ct                         42

<210> SEQ ID NO 113
<211> LENGTH: 38
<212> TYPE: DNA
<213> ORGANISM: Artificial
<220> FEATURE:
<223> OTHER INFORMATION: PCR primer

<400> SEQUENCE: 113
tccctcacag tctcagaaaa gcccaggggc taatgact                              38

<210> SEQ ID NO 114
<211> LENGTH: 59
<212> TYPE: DNA
<213> ORGANISM: Artificial
<220> FEATURE:
<223> OTHER INFORMATION: PCR primer

<400> SEQUENCE: 114
tccctcacag tctcagaaaa ggtagcgttg ctatcacctg cgcccagggg ctaatgact       59

<210> SEQ ID NO 115
<211> LENGTH: 39
<212> TYPE: DNA
<213> ORGANISM: Artificial
<220> FEATURE:
<223> OTHER INFORMATION: PCR primer

<400> SEQUENCE: 115
tccctcacag tctcagaaaa gccccagggg ctaatgact                             39

<210> SEQ ID NO 116
<211> LENGTH: 59
<212> TYPE: DNA
<213> ORGANISM: Artificial
<220> FEATURE:
<223> OTHER INFORMATION: PCR primer

<400> SEQUENCE: 116
tccctcacag tctcagaaaa ggtagcgttg ctatcacctg cgcccagggg ctaatgact       59

<210> SEQ ID NO 117
```

```
<211> LENGTH: 39
<212> TYPE: DNA
<213> ORGANISM: Artificial
<220> FEATURE:
<223> OTHER INFORMATION: PCR primer

<400> SEQUENCE: 117
tccctcacag tctcagaaaa gccccagggg ctaatgact                    39

<210> SEQ ID NO 118
<211> LENGTH: 61
<212> TYPE: DNA
<213> ORGANISM: Artificial
<220> FEATURE:
<223> OTHER INFORMATION: PCR primer

<400> SEQUENCE: 118
tccctcacag tctcagaaaa gggtagcgtt gctatcacct gcgcccagg ggctaatgac    60 t                                                             61

<210> SEQ ID NO 119
<211> LENGTH: 20
<212> TYPE: DNA
<213> ORGANISM: Artificial
<220> FEATURE:
<223> OTHER INFORMATION: PCR primer

<400> SEQUENCE: 119
tccctcacag tctaatgact                                         20

<210> SEQ ID NO 120
<211> LENGTH: 59
<212> TYPE: DNA
<213> ORGANISM: Artificial
<220> FEATURE:
<223> OTHER INFORMATION: PCR primer

<400> SEQUENCE: 120
tccctcacag tctcagaaaa ggtagcgttg ctatcacctg cgcccagggg ctaatgact    59
```

LARGE GENE EXCISION AND INSERTION

RELATED APPLICATION DATA

This application claims priority to U.S. Provisional Patent Application No. 61/906,188 filed on Nov. 19, 2013 and is hereby incorporated herein by reference in its entirety for all purposes.

STATEMENT OF GOVERNMENT INTERESTS

This invention was made with government support under Grant No. P50 HG005550 awarded by the National Institutes of Health. The government has certain rights in the invention.

BACKGROUND

Bacterial and archaeal CRISPR-Cas systems rely on short guide RNAs in complex with Cas proteins to direct degradation of complementary sequences present within invading foreign nucleic acid. See Deltcheva, E. et al. CRISPR RNA maturation by trans-encoded small RNA and host factor RNase III. *Nature* 471, 602-607 (2011); Gasiunas, G., Barrangou, R., Horvath, P. & Siksnys, V. Cas9-crRNA ribonucleoprotein complex mediates specific DNA cleavage for adaptive immunity in bacteria. *Proceedings of the National Academy of Sciences of the United States of America* 109, E2579-2586 (2012); Jinek, M. et al. A programmable dual-RNA-guided DNA endonuclease in adaptive bacterial immunity. *Science* 337, 816-821 (2012); Sapranauskas, R. et al. The *Streptococcus thermophilus* CRISPR/Cas system provides immunity in *Escherichia coli. Nucleic acids research* 39, 9275-9282 (2011); and Bhaya, D., Davison, M. & Barrangou, R. CRISPR-Cas systems in bacteria and archaea: versatile small RNAs for adaptive defense and regulation. *Annual review of genetics* 45, 273-297 (2011). A recent in vitro reconstitution of the *S. pyogenes* type II CRISPR system demonstrated that crRNA ("CRISPR RNA") fused to a normally trans-encoded tracrRNA ("trans-activating CRISPR RNA") is sufficient to direct Cas9 protein to sequence-specifically cleave target DNA sequences matching the crRNA. Expressing a gRNA homologous to a target site results in Cas9 recruitment and degradation of the target DNA. See H. Deveau et al., Phage response to CRISPR-encoded resistance in *Streptococcus thermophilus*. *Journal of Bacteriology* 190, 1390 (February, 2008).

SUMMARY

Aspects of the present disclosure are directed to improving efficiency of large gene insertions into a target nucleic acid. Aspects of the present disclosure are directed to the excision of a large nucleic acid sequence, such as a large gene, from a target nucleic acid within a cell. Aspects of the present disclosure are directed to the insertion of a large nucleic acid sequence, such as a large gene, into a target nucleic acid within a cell. Aspects of the present disclosure are directed to the excision of a large nucleic acid sequence, such as a large gene, from a target nucleic acid within a cell and insertion of a large nucleic acid sequence, such as a large gene, into the target nucleic acid within the cell.

Aspects of the present disclosure are directed to the design of targeting vectors for large nucleic acid replacements within a target nucleic acid.

According to certain aspects, a DNA binding protein, such as a sequence specific nuclease, is used to create a double stranded break in the target nucleic acid sequence. One or more or a plurality of double stranded breaks may be made in the target nucleic acid sequence. According to one aspect, a first nucleic acid sequence is removed from the target nucleic acid sequence and an exogenous nucleic acid sequence is inserted into the target nucleic acid sequence between the cut sites or cut ends of the target nucleic acid sequence. According to certain aspects, a double stranded break at each homology arm increases or improves efficiency of nucleic acid sequence insertion or replacement, such as by homologous recombination. According to certain aspects, multiple double stranded breaks or cut sites improve efficiency of incorporation of a nucleic acid sequence from a targeting vector.

Certain aspects of the present disclosure are directed to methods of homozygous knock-in targeted replacement and excision of multi-kilobase endogenous genes in cells, such as mammalian cells, including human induced pluripotent stem cells (iPSC). According to certain aspects, the methods are practiced without a selection marker.

According to certain aspects, methods are provided for the insertion of a large gene into a target nucleic acid sequence using DNA binding protein having nuclease activity, such as an RNA guided DNA binding protein having nuclease activity. According to certain aspects, a first foreign nucleic acid encoding one or more RNAs (ribonucleic acids) complementary to DNA (deoxyribonucleic acid) is introduced into a cell, wherein the DNA includes the target nucleic acid. A second foreign nucleic acid encoding an RNA guided DNA binding protein having nuclease activity that binds to the DNA and is guided by the one or more RNAs is introduced into the cell. The one or more RNAs and the RNA guided DNA binding protein are expressed, wherein the one or more RNAs and the RNA guided DNA binding protein co-localize to the DNA and wherein the DNA binding protein cuts the target nucleic acid to remove a first nucleic acid sequence of interest. An exogenous nucleic acid sequence of interest is inserted into the target nucleic acid sequence between the cut sites resulting in the removal of the first nucleic acid sequence of interest. According to certain aspects, multiple guide RNAs may be used.

Large nucleic acid sequences within the scope of the present disclosure (which may be the first nucleic acid sequence of interest to be removed or the exogenous nucleic acid sequence to be inserted) are nucleic acid sequences having between greater than 100 base pairs to about 100,000 base pairs, between greater than 100 base pairs and about 10,000 base pairs in length, between about 200 base pairs to about 100,000 base pairs, between about 300 base pairs to about 100,000 base pairs, between about 400 base pairs to about 100,000 base pairs, between about 500 base pairs to about 100,000 base pairs, between about 600 base pairs to about 100,000 base pairs, between about 700 base pairs to about 100,000 base pairs, between about 800 base pairs to about 100,000 base pairs, between about 900 base pairs to about 100,000 base pairs, between about 1000 base pairs to about 100,000 base pairs, between about 2000 base pairs to about 100,000 base pairs, between about 3000 base pairs to about 100,000 base pairs, between about 4000 base pairs to about 100,000 base pairs, between about 5000 base pairs to about 100,000 base pairs, between about 6000 base pairs to about 100,000 base pairs, between about 7000 base pairs to about 100,000 base pairs, between about 8000 base pairs to about 100,000 base pairs, between about 9000 base pairs to about 100,000 base pairs, between about 10,000 base pairs to about 100,000 base pairs, between about 20,000 base pairs to about 100,000 base pairs, between about 30,000 base pairs to about 100,000 base pairs, between about 40,000 base pairs to about 100,000 base pairs, between about 50,000 base pairs to about 100,000 base pairs, between about 60,000 base pairs to about 100,000 base pairs, between about 70,000 base pairs to about 100,000 base pairs, between about 80,000 base pairs to about 100,000 base pairs, between about 90,000 base pairs to about 100,000 base pairs, between about 500 base pairs to about 10,000 base pairs, between about 1000 base pairs to about 10,000 base pairs, between about 2000 base pairs to about 10,000 base pairs or between about 1000 base pairs to about 5,000 base pairs. Large nucleic acid sequences may be referred to herein as "kilobase", or "multi-kilobase" nucleic acid sequences, i.e. greater than 1000 base pairs. According to certain aspects, the large nucleic acids are greater than 1000 base pairs. According to certain aspects, the nucleic acid sequence to be inserted is heterologous to the genome of the cell into which it is to be inserted. According to certain aspects, the exogenous nucleic acid being inserted into the target nucleic acid sequence is a foreign nucleic acid sequence which may be different from the first nucleic acid sequence of interest that it is replacing or may be different from any nucleic acid sequence in the target nucleic acid or genome of the cell. According to one aspect, the removal of the first nucleic acid sequence of interest and the insertion of the exogenous nucleic acid occurs simultaneously or substantially simultaneously. This is to be distinguished from methods where a deletion occurs which is followed by a separate insertion.

According to certain aspects, a targeting vector is provided containing a foreign sequence which is used to engineer a gene replacement using a single cut site positioned at one side of the replacement. The foreign sequence is flanked by sequences identical to the genome around the replacement. Then, gene replacement can be done with only one cut at one side. The other end will be resolved by natural recombination between the genome and its complementary sequence that was placed around the foreign sequence in the targeting vector (the homology arm). However, aspects of the present disclosure also include cutting both sides of the replaced region.

According to one aspect, the cell is a eukaryotic cell. According to one aspect, the cell is a yeast cell, a plant cell or an animal cell. According to one aspect, the cell is a mammalian cell.

According to one aspect, the RNA is between about 10 to about 500 nucleotides. According to one aspect, the RNA is between about 20 to about 100 nucleotides.

According to one aspect, the one or more RNAs is a guide RNA. According to one aspect, the one or more RNAs is a crRNA. According to one aspect, the one or more RNAs is a tracrRNA. According to one aspect, the one or more RNAs is a tracrRNA-crRNA fusion.

According to one aspect, the DNA is genomic DNA, mitochondrial DNA, viral DNA, or exogenous DNA.

According to one aspect, the RNA guided DNA binding protein is of a Type II CRISPR System that binds to the DNA and is guided by the one or more RNAs. According to one aspect, the RNA guided DNA binding protein is a Cas9 protein that binds to the DNA and is guided by the one or more RNAs.

Further features and advantages of certain embodiments of the present invention will become more fully apparent in the following description of embodiments and drawings thereof, and from the claims.

BRIEF DESCRIPTION OF THE DRAWINGS

The foregoing and other features and advantages of the present embodiments will be more fully understood from the following detailed description of illustrative embodiments taken in conjunction with the accompanying drawings in which:

FIG. 1(a) Two Crispr sgRNAs target hThy1 within intron 1 (L1) or after the polyadenylation sites (R1). The mThy1 targeting vector plasmid contains mThy1 exons 2 and 3 (orange), flanked by hThy1 homology arms outside the sgRNA sites—the hThy1 promoter and exon 1 (which encodes the leader sequence) are retained but the sgRNA sites are disrupted. Small triangles indicate the primer sites for the four genotyping PCR reactions. FIG. 1(b) PGP1 iPSC were nucleofected with plasmids encoding the mThy1 targeting vector, the Cas9 nuclease, and L1, R1, both, or no sgRNAs. Five days later, cells were analyzed by flow cytometry. The percentage of cells that have gained mThy1 expression and/or lost hThy1 expression are indicated. FIG. 1(c) Single iPSC were FACS sorted from each quadrant, cultured in individual wells, and genotyped using the four PCR reactions. Alleles were identified based on the size and Sanger sequencing of the PCR products: native human (+); recombined mouse (m); excised between the two sgRNA sites (Δ); and inverted between the two sgRNA sites (i). Representative gels from +/+ wild type, m/+ heterozygous, m/m homozygous, m/Δ heterozygous, Δ/Δ homozygous, and i/Δ heterozygous colonies are shown. FIG. 1(d) Frequency of genotypes among FACS-sorted iPS colonies. Results are representative of three independent experiments.

FIG. 2(a) Crispr sgRNAs were generated targeting the human Thy1 gene: two within intron 1 (Left: L1 and L2), and ten at various distances after hThy1 (Right: R1 through R10). b+c) Pairs of one left and one right sgRNA were nucleofected into either FIG. 2(b) PGP1 iPSC or FIG. 2(c) a Thy1$^{m/+}$ PGP1 iPSC clone. As a negative control, only a left sgRNA was nucleofected (right column) Five days later, cells were analyzed by flow cytometry for either FIG. 2(b) homozygous deletion of both human Thy1 alleles or FIG. 2(c) heterozygous deletion of the remaining human Thy1 allele and retention of the mouse Thy1 allele. The distance between the sgRNA sites (Thy1 Δ) and the frequency of hThy1$^-$ cells is indicated. FIG. 2(d)-(e) The percent of hThy1$^-$ cells from each sgRNA pair minus that from the left sgRNA-only control is plotted against the size of the Thy1 deletion. sgRNA pairs that included L1 or L2 are shown in black or red, respectively. Error bars show mean±s.e.m of two independent experiments.

FIG. 3(a) Native sequence of the human Thy1 locus (SEQ ID NO:108). Crispr sgRNA targeting sites L1 (purple) and R1 (red) lie 2.7 kb apart on the human Thy1 locus. The predicted nuclease cleavage sites are indicated 6 bp upstream of the PAM (underlined). FIG. 3(b)-(c) Biallelic sequences of FIG. 3(b) four Δ/Δ double-excised (SEQ ID NOs:109-112) and FIG. 3(c) five i/Δ inverted-and-excised (SEQ ID NOs:113-120) hThy1- mThy1- colonies described in FIG. 1d. Sequences that were found in two separate clones are indicated as x2. Results are representative of two independent experiments.

FIG. 4(a) Two Crispr sgRNAs were designed 9.8 kb apart that target the human CD147 gene within intron 1 (L147, left) and after the polyadenylation site (R147, right). The mouse CD147 targeting vector plasmid consists of a 5.8 kb sequence encompassing mouse CD147 exons 2-7 (brown), flanked by homology arms that match the human CD147 sequence outside the sgRNA sites. In the targeting construct, the human CD147 promoter and exon 1 (which encodes the leader sequence) are retained but the sgRNA sites are disrupted. FIG. 4(b) PGP1 iPSC were nucleofected with plasmids encoding the mouse CD147 targeting vector, the Cas9 nuclease, and either, both, or no sgRNAs. Nine days later, cells were analyzed by flow cytometry. The percentage of cells that have gained expression of mouse CD147 and/or lost expression of human CD147 are indicated. Results are representative of three independent experiments.

FIG. 5(a) Two Crispr sgRNAs were designed 2.2 kb apart that target the human Thy1 gene within exon 2 (L3, left) and after the polyadenylation sites (R1, right). Two TALEN pairs were also designed that target the same L3 and R1 sites. For the "knock-in" targeting vector, a 1.9 kb sequence encompassing the fluorescent mCherry gene under the constitutive pGK promoter (red) was flanked with homology arms that match the human Thy1 sequence outside the sgRNA sites. The pGK-mCherry insert was cloned in either the forward or reverse orientation relative to the Thy1 gene. The sgRNA and TALEN sites are disrupted in both mCherry targeting constructs. FIG. 5(b) PGP1 iPSC were nucleofected with the sense or antisense mCherry targeting vector along with plasmids encoding: the Cas9 nuclease with either or both sgRNAs; either or both TALEN pairs; or an empty vector plasmid. Ten days later, cells were analyzed by flow cytometry. The percentage of cells that have gained expression of mCherry and/or lost expression of human Thy1 are indicated. Results are representative of two independent experiments.

FIG. 6(a) The circular plasmid mouse Thy1 targeting vector from FIG. 1 was amplified using PCR primers at the ends of the homology arms (small triangles) to produce a linear form of the mouse Thy1 targeting vector. FIG. 6(b) PGP1 iPSC were nucleofected with the circular plasmid or the linear PCR product mouse Thy1 targeting vector along with plasmids encoding the Cas9 nuclease, and L1, R1, both, or no sgRNAs. Six days later, cells were analyzed by flow cytometry. The frequency of cells that have gained expression of mouse Thy1 and/or lost expression of human Thy1 are indicated. Results are representative of two independent experiments.

FIG. 8(a)-(c). Targeted gene replacement with homology on either side of each cut site. FIG. 8(a) The mThy1 targeting vector from FIG. 1 (Outside) was modified such that the human Thy1 homology arms extend inside the L1 and R1 sgRNA sites. While mouse Thy1 exons 2 and 3 (orange) are completely retained in this targeting vector, 350 bp of mouse Thy1 intron 1 and 150 bp of mouse Thy1 sequence after the polyadenylation site was replaced with the corresponding human sequence. The resulting targeting vector contains intact L1 and R1 sgRNA sites (Intact). Next, a single base pair was deleted from each sgRNA site in the targeting vector to develop a alternate version with similar homology arms but disrupted sgRNA sites (Disrupted). FIG. 8(b)-(c) PGP1 or PGP4 iPSC were nucleofected with one of the mouse Thy1 targeting vectors (Outside, Intact, or Disrupted) along with plasmids encoding the Cas9 nuclease, and L1, R1, both, or no sgRNAs. FIG. 8(b) Two days post nucleofection, a cell sample of each condition was stained with the viability dye ToPro3, and analyzed by flow cytometry using a constant flow rate and collection time. Viable cell counts were normalized to that of the Outside mouse Thy1 targeting vector with no sgRNA (100). FIG. 8(c) Five days post nucleofection, cells were analyzed by flow cytometry. The percentage of cells that have gained expression of mouse Thy1 and/or lost expression of human Thy1 are indicated. Results are representative of three (PGP1) and two (PGP4) independent experiments.

DETAILED DESCRIPTION

Figure 1:
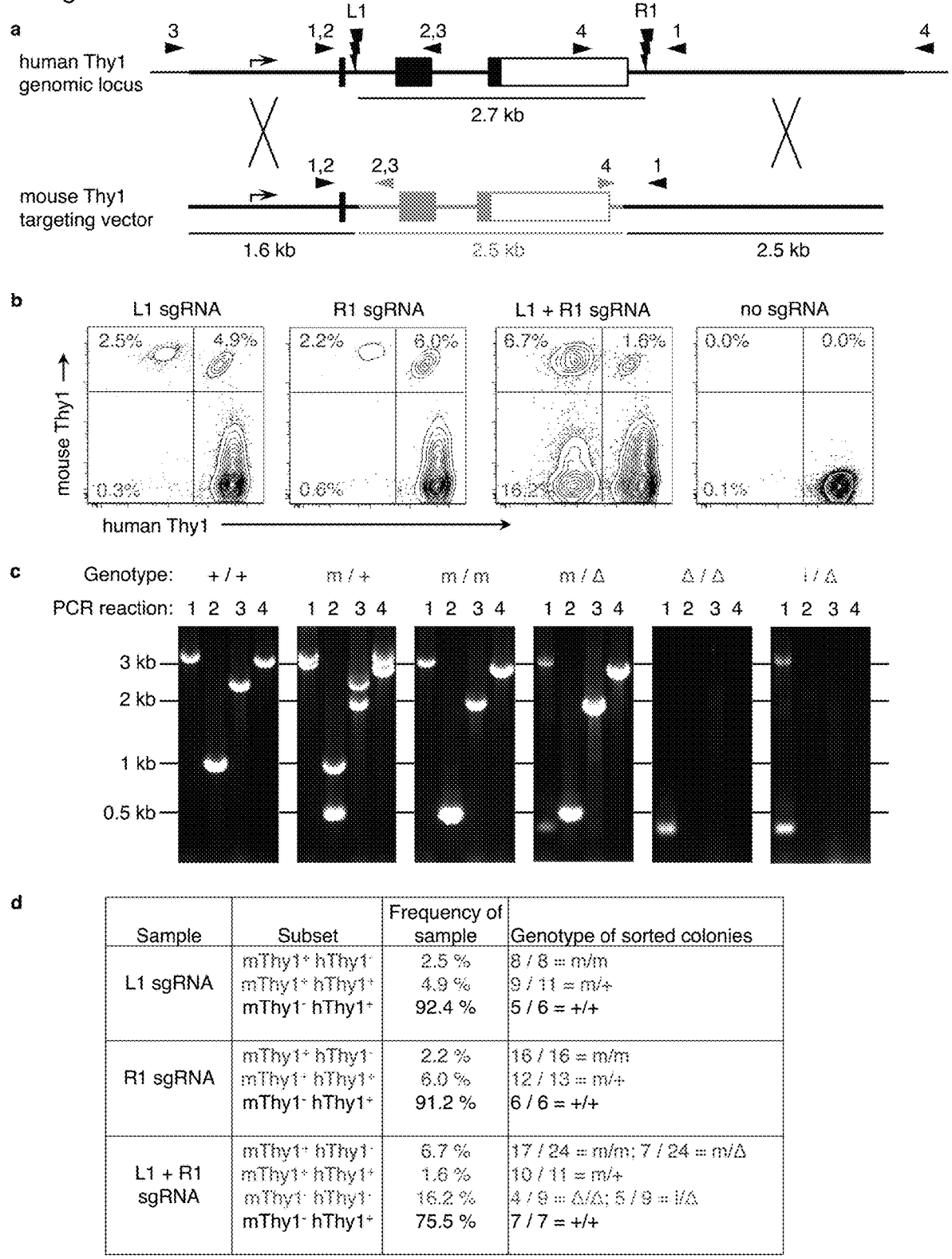
FIG. 1(a)-(d) Homozygous targeted gene replacement using one or two CRISPR sgRNAs.
Figure 2:
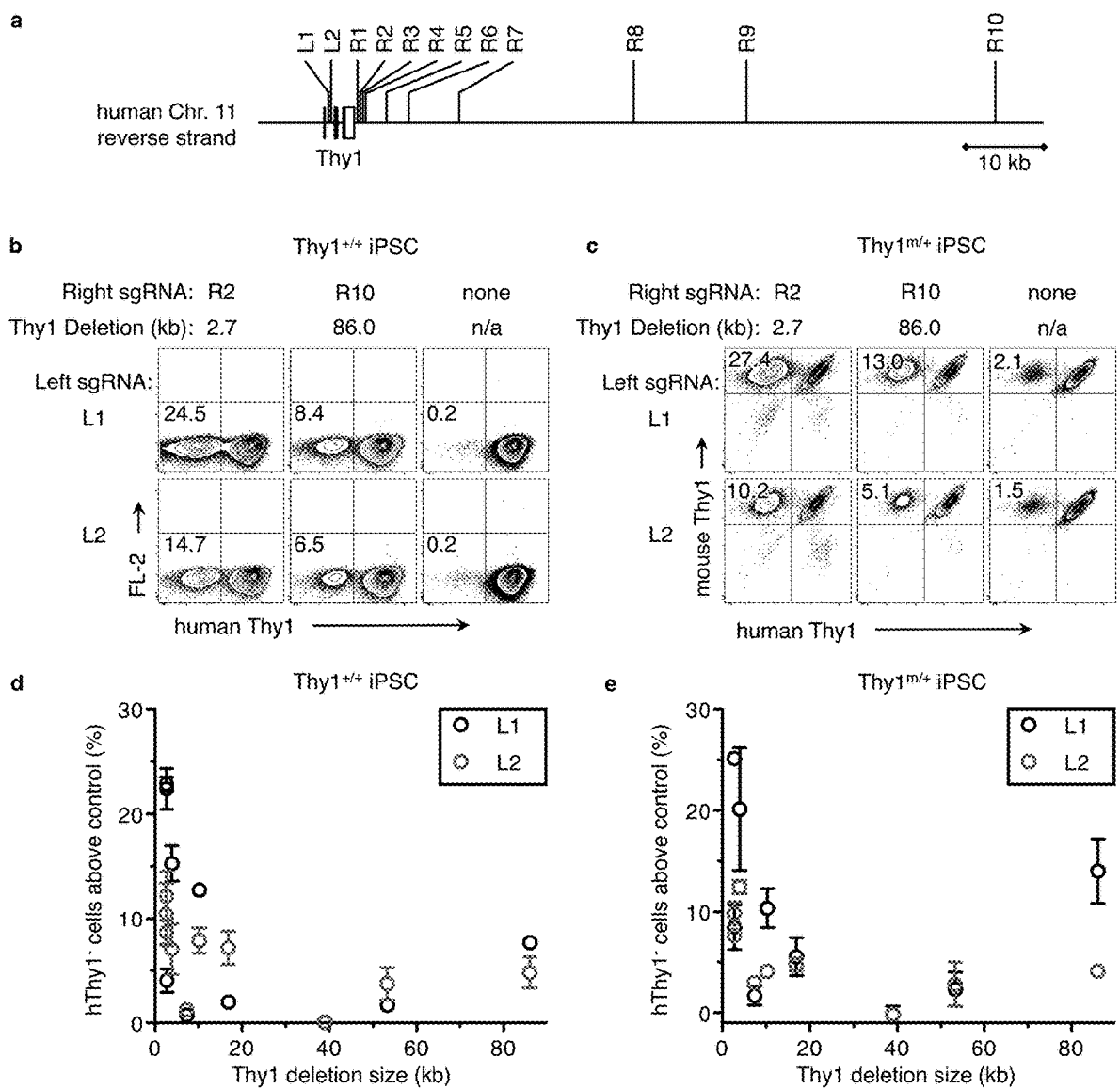
FIG. 2(a)-(e). Frequency of CRISPR-generated homozygous and heterozygous deletions.
Figure 3:
FIG. 3(a)-(c). Sequences of excision and inversion junctions. Genotyping PCR reaction #1 was performed on genomic DNA purified from FACS-sorted hThy1- mThy1- iPSC clones (as described in FIG. 1) and analyzed by Sanger sequencing using the same PCR primers. Double peaks in the resulting Sanger sequencing traces were deconvoluted to reveal the biallelic sequence of each clone.
Figure 4:
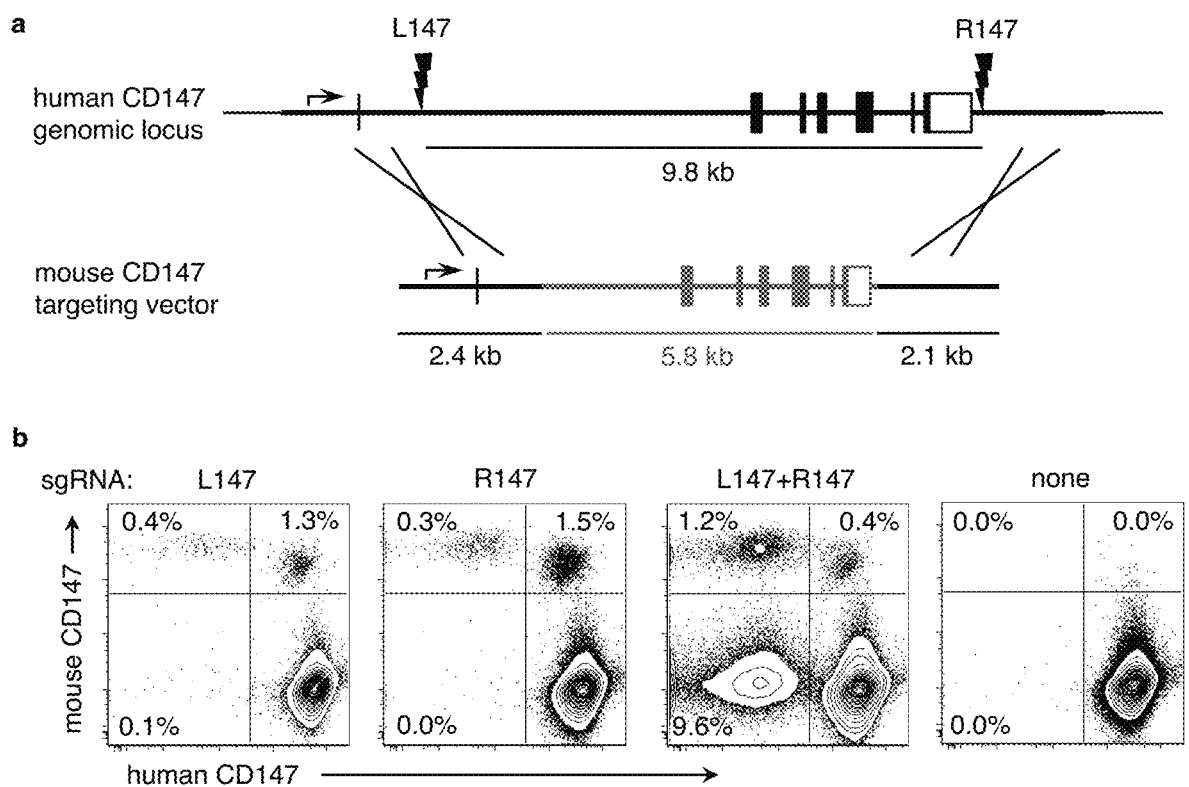
FIG. 4(a)-(b). Targeted replacement of the mouse CD147 gene into the human CD147 genomic locus.

Embodiments of the present disclosure are based on the use of DNA binding proteins having nuclease activity to remove a first nucleic acid sequence from a target nucleic acid sequence thereby allowing insertion of an exogenous nucleic acid sequence therein. Such DNA binding proteins are readily known to those of skill in the art to bind to DNA for various purposes. Such DNA binding proteins may be naturally occurring. DNA binding proteins included within the scope of the present disclosure include those which may be guided by RNA, referred to herein as guide RNA. According to this aspect, the guide RNA and the RNA guided DNA binding protein form a co-localization complex at the DNA. Such DNA binding proteins having nuclease activity are known to those of skill in the art, and include naturally occurring DNA binding proteins having nuclease activity, such as Cas9 proteins present, for example, in Type II CRISPR systems. Such Cas9 proteins and Type II CRISPR systems are well documented in the art. See Makarova et al., *Nature Reviews, Microbiology*, Vol. 9, June 2011, pp. 467-477 including all supplementary information hereby incorporated by reference in its entirety.

Exemplary DNA binding proteins having nuclease activity function to nick or cut double stranded DNA. Such nuclease activity may result from the DNA binding protein having one or more polypeptide sequences exhibiting nuclease activity. Such exemplary DNA binding proteins may have two separate nuclease domains with each domain responsible for cutting or nicking a particular strand of the double stranded DNA. Exemplary polypeptide sequences having nuclease activity known to those of skill in the art include the McrA-HNH nuclease related domain and the RuvC-like nuclease domain. Accordingly, exemplary DNA binding proteins are those that in nature contain one or more of the McrA-HNH nuclease related domain and the RuvC-like nuclease domain.

According to one aspect, a DNA binding protein having two or more nuclease domains may be modified or altered to inactivate all but one of the nuclease domains. Such a modified or altered DNA binding protein is referred to as a DNA binding protein nickase, to the extent that the DNA binding protein cuts or nicks only one strand of double stranded DNA. When guided by RNA to DNA, the DNA binding protein nickase is referred to as an RNA guided DNA binding protein nickase.

An exemplary DNA binding protein is an RNA guided DNA binding protein of a Type II CRISPR System. An exemplary DNA binding protein is a Cas9 protein.

In *S. pyogenes*, Cas9 generates a blunt-ended double-stranded break 3 bp upstream of the protospacer-adjacent motif (PAM) via a process mediated by two catalytic domains in the protein: an HNH domain that cleaves the complementary strand of the DNA and a RuvC-like domain that cleaves the non-complementary strand. See Jinke et al., *Science* 337, 816-821 (2012) hereby incorporated by reference in its entirety. Cas9 proteins are known to exist in many Type II CRISPR systems including the following as identified in the supplementary information to Makarova et al., Nature Reviews, Microbiology, Vol. 9, June 2011, pp. 467-477: *Methanococcus maripaludis* C7; *Corynebacterium diphtheriae*; *Corynebacterium efficiens* YS-314; *Corynebacterium glutamicum* ATCC 13032 Kitasato; *Corynebacterium glutamicum* ATCC 13032 Bielefeld; *Corynebacterium glutamicum* R; *Corynebacterium kroppenstedtii* DSM 44385; *Mycobacterium abscessus* ATCC 19977; *Nocardia farcinica* IFM10152; *Rhodococcus erythropolis* PR4; *Rhodococcus jostii* RHA1; *Rhodococcus opacus* B4 uid36573; *Acidothermus cellulolyticus* 11B; *Arthrobacter chlorophenolicus* A6; *Kribbella flavida* DSM 17836 uid43465; *Thermomonospora curvata* DSM 43183; *Bifidobacterium dentium* Bd1; *Bifidobacterium longum* DJO10A; *Slackia heliotrinireducens* DSM 20476; *Persephonella marina* EX H1; *Bacteroides fragilis* NCTC 9434; *Capnocytophaga ochracea* DSM 7271; *Flavobacterium psychrophilum* JIP02 86; *Akkermansia muciniphila* ATCC BAA 835; *Roseiflexus castenholzii* DSM 13941; Roseiflexus RS1; *Synechocystis* PCC6803; *Elusimicrobium minutum* Pei191; uncultured Termite group 1 bacterium phylotype Rs D17; *Fibrobacter succinogenes* S85; *Bacillus cereus* ATCC 10987; *Listeria innocua*; *Lactobacillus casei*; *Lactobacillus rhamnosus* GG; *Lactobacillus salivarius* UCC118; *Streptococcus agalactiae* A909; *Streptococcus agalactiae* NEM316; *Streptococcus agalactiae* 2603; *Streptococcus dysgalactiae equisimilis* GGS 124; *Streptococcus equi zooepidemicus* MGCS10565; *Streptococcus gallolyticus* UCN34 uid46061; *Streptococcus gordonii* Challis subst CH1; *Streptococcus mutans* NN2025 uid46353; *Streptococcus mutans*; *Streptococcus pyogenes* M1 GAS; *Streptococcus pyogenes* MGAS5005; *Streptococcus pyogenes* MGAS2096; *Streptococcus pyogenes* MGAS9429; *Streptococcus pyogenes* MGAS10270; *Streptococcus pyogenes* MGAS6180; *Streptococcus pyogenes* MGAS315; *Streptococcus pyogenes* SSI-1; *Streptococcus pyogenes* MGAS10750; *Streptococcus pyogenes* NZ131; *Streptococcus thermophiles* CNRZ1066; *Streptococcus thermophiles* LMD-9; *Streptococcus thermophiles* LMG 18311; *Clostridium botulinum* A3 Loch Maree; *Clostridium botulinum* B Eklund 17B; *Clostridium botulinum* Ba4 657; *Clostridium botulinum* F Langeland; *Clostridium cellulolyticum* H10; *Finegoldia magna* ATCC 29328; *Eubacterium rectale* ATCC 33656; *Mycoplasma gallisepticum*; *Mycoplasma mobile* 163K; *Mycoplasma penetrans*; *Mycoplasma synoviae* 53; *Streptobacillus moniliformis* DSM 12112; *Bradyrhizobium* BTAi1; *Nitrobacter hamburgensis* X14; *Rhodopseudomonas palustris* BisB18; *Rhodopseudomonas palustris* BisB5; *Parvibaculum lavamentivorans* DS-1; *Dinoroseobacter shibae* DFL 12; *Gluconacetobacter diazotrophicus* Pal 5 FAPERJ; *Gluconacetobacter diazotrophicus* Pal 5 JGI; *Azospirillum* B510 uid46085; *Rhodospirillum rubrum* ATCC 11170; *Diaphorobacter* TPSY uid29975; *Verminephrobacter eiseniae* EF01-2; *Neisseria meningitides* 053442; *Neisseria meningitides* alpha 14; *Neisseria meningitides* Z2491; *Desulfovibrio salexigens* DSM 2638; *Campylobacter jejuni doylei* 269 97; *Campylobacter jejuni* 81116; *Campylobacter jejuni*; *Campylobacter lari* RM2100; *Helicobacter hepaticus*; *Wolinella succinogenes*; *Tolumonas auensis* DSM 9187; *Pseudoalteromonas atlantica* T6c; *Shewanella pealeana* ATCC 700345; *Legionella pneumophila* Paris; *Actinobacillus succinogenes* 130Z; *Pasteurella multocida*; *Francisella tularensis novicida* U112; *Francisella tularensis holarctica*; *Francisella tularensis* FSC 198; *Francisella tularensis tularensis*; *Francisella tularensis* WY96-3418; and *Treponema denticola* ATCC 35405. Accordingly, aspects of the present disclosure are directed to a Cas9 protein present in a Type II CRISPR system.

The Cas9 protein may be referred by one of skill in the art in the literature as Csn1. The *S. pyogenes* Cas9 protein sequence that is the subject of experiments described herein is shown below. See Deltcheva et al., *Nature* 471, 602-607 (2011) hereby incorporated by reference in its entirety.

```
                                            (SEQ ID NO: 1)
MDKKYSIGLDIGTNSVGWAVITDEYKVPSKKFKVLGNTDRHSIKKNLIGAL

LFDSGETAEATRLKRTARRRYTRRKNRICYLQEIFSNEMAKVDDSFFHRLE

ESFLVEEDKKHERHPIFGNIVDEVAYHEKYPTIYHLRKKLVDSTDKADLRL

IYLALAHMIKFRGHFLIEGDLNPDNSDVDKLFIQLVQTYNQLFEENPINAS

GVDAKAILSARLSKSRRLENLIAQLPGEKKNGLFGNLIALSLGLTPNFKSN

FDLAEDAKLQLSKDTYDDDLDNLLAQIGDQYADLFLAAKNLSDAILLSDIL

RVNTEITKAPLSASMIKRYDEHHQDLTLLKALVRQQLPEKYKEIFFDQSKN

GYAGYIDGGASQEEFYKFIKPILEKMDGTEELLVKLNREDLLRKQRTFDNG

SIPHQIHLGELHAILRRQEDFYPFLKDNREKIEKILTFRIPYYVGPLARGN

SRFAWMTRKSEETITPWNFEEVVDKGASAQSFIERMTNFDKNLPNEKVLPK

HSLLYEYFTVYNELTKVKYVTEGMRKPAFLSGEQKKAIVDLLFKTNRKVTV

KQLKEDYFKKIECFDSVEISGVEDRFNASLGTYHDLLKIIKDKDFLDNEEN

EDILEDIVLTLTLFEDREMIEERLKTYAHLFDDKVMKQLKRRRYTGWGRLS

RKLINGIRDKQSGKTILDFLKSDGFANRNFMQLIHDDSLTFKEDIQKAQVS

GQGDSLHEHIANLAGSPAIKKGILQTVKVVDELVKVMGRHKPENIVIEMAR

ENQTTQKGQKNSRERMKRIEEGIKELGSQILKEHPVENTQLQNEKLYLYYL

QNGRDMYVDQELDINRLSDYDVDHIVPQSFLKDDSIDNKVLTRSDKNRGKS

DNVPSEEVVKKMKNYWRQLLNAKLITQRKFDNLTKAERGGLSELDKAGFIK

RQLVETRQITKHVAQILDSRMNTKYDENDKLIREVKVITLKSKLVSDFRKD

FQFYKVREINNYHHAHDAYLNAVVGTALIKKYPKLESEFVYGDYKVYDVRK

MIAKSEQEIGKATAKYFFYSNIMNFFKTEITLANGEIRKRPLIETNGETGE

IVWDKGRDFATVRKVLSMPQVNIVKKTEVQTGGFSKESILPKRNSDKLIAR

KKDWDPKKYGGFDSPTVAYSVLVVAKVEKGKSKKLKSVKELLGITIMERSS

FEKNPIDFLEAKGYKEVKKDLIIKLPKYSLFELENGRKRMLASAGELQKGN

ELALPSKYVNFLYLASHYEKLKGSPEDNEQKQLFVEQHKHYLDEIIEQISE

FSKRVILADANLDKVLSAYNKHRDKPIREQAENIIHLFTLTNLGAPAAFKY

FDTTIDRKRYTSTKEVLDATLIHQSITGLYETRIDLSQLGGD-
```

According to one aspect, the DNA binding protein nucleases include homologs and orthologs thereof and protein sequences having at least 30%, 40%, 50%, 60%, 70%, 80%, 90%, 95%, 98% or 99% homology thereto and being a DNA binding protein with nuclease activity.

Further aspects of the present disclosure are directed to the use of DNA binding proteins or systems in general for the genetic modification or editing of a target nucleic acid, such as a target gene, such as by insertion of a larger gene into the target nucleic acid. One of skill in the art will readily identify exemplary DNA binding systems based on the present disclosure. Such DNA binding systems include ZFN, TALE, TALENS or CRISPR/Cas9 nucleases.

According to certain aspects, methods are described herein of editing nucleic acids in a cell that include introducing one or more, two or more or a plurality of foreign nucleic acids into the cell. The foreign nucleic acids introduced into the cell encode for a guide RNA or guide RNAs, a Cas9 protein or proteins and the large nucleic acid sequence to be inserted. Together, a guide RNA and a Cas9 protein are referred to as a co-localization complex as that term is understood by one of skill in the art to the extent that the guide RNA and the Cas9 protein bind to DNA and the Cas9 protein cuts the DNA to remove a first nucleic acid sequence of interest. The large nucleic acid sequence is inserted into the DNA. According to certain additional aspects, the foreign nucleic acids introduced into the cell encode for a guide RNA or guide RNAs and a Cas9 protein.

Cells according to the present disclosure include any cell into which foreign nucleic acids can be introduced and expressed as described herein. It is to be understood that the basic concepts of the present disclosure described herein are not limited by cell type. Cells according to the present disclosure include eukaryotic cells, prokaryotic cells, animal cells, plant cells, fungal cells, archael cells, eubacterial cells and the like. Cells include eukaryotic cells such as yeast cells, plant cells, and animal cells. Particular cells include mammalian cells. Particular cells include stem cells, such as pluripotent stem cells, such as human induced pluripotent stem cells.

Target nucleic acids include any nucleic acid sequence to which a DNA binding protein nuclease can be useful to nick or cut, such as a RNA guided DNA binding protein which forms a co-localization complex as described herein. Target nucleic acids include genes. For purposes of the present disclosure, DNA, such as double stranded DNA, can include the target nucleic acid and a co-localization complex can bind to or otherwise co-localize with the DNA at or adjacent or near the target nucleic acid and in a manner in which the co-localization complex may have a desired effect on the target nucleic acid. Such target nucleic acids can include endogenous (or naturally occurring) nucleic acids and exogenous (or foreign) nucleic acids. One of skill based on the present disclosure will readily be able to identify or design guide RNAs and Cas9 proteins which co-localize to a DNA including a target nucleic acid. DNA includes genomic DNA, mitochondrial DNA, viral DNA or exogenous DNA.

Foreign nucleic acids (i.e. those which are not part of a cell's natural nucleic acid composition) may be introduced into a cell using any method known to those skilled in the art for such introduction. Such methods include transfection, transduction, viral transduction, microinjection, lipofection, nucleofection, nanoparticle bombardment, transformation, conjugation and the like. One of skill in the art will readily understand and adapt such methods using readily identifiable literature sources.

The following examples are set forth as being representative of the present disclosure. These examples are not to be construed as limiting the scope of the present disclosure as these and other equivalent embodiments will be apparent in view of the present disclosure, figures and accompanying claims.

EXAMPLE I sgRNA Target Sequences

A computational algorithm was used to identify sgRNA (single guide RNA) sequences {Mali:2013eu} at various positions around the human Thy1 and CD147 genes based on their uniqueness in the human genome:

```
Human Thy1:
L1
                                          (SEQ ID NO: 2)
CACAG TCTCA GAAAA GCGC AGG L2
                                          (SEQ ID NO: 3)
AAATA TCAGC GCGGT GGAT TGG L3
                                          (SEQ ID NO: 4)
GGTCA GGCTG AACTC GTAC TGG R1
                                          (SEQ ID NO: 5)
TTAGT AGCAA CGCTA CCCC AGG
R2
                                          (SEQ ID NO: 6)
GTGTG CAGTC ATTAG CCCC TGG R3
                                          (SEQ ID NO: 7)
GGGCA AATGT GTCTC GTTA GGG R4
                                          (SEQ ID NO: 8)
TTCTC CTTTC CGAAG TCCG TGG R5
                                          (SEQ ID NO: 9)
GCCGC TGTCG CCTGG CAAA AGG R6
                                         (SEQ ID NO: 10)
GATGG TAGAC ATCGA CCAT GGG R7
                                         (SEQ ID NO: 11)
TTCAA TTTCG GGCCC GATC TGG R8
                                         (SEQ ID NO: 12)
TGAGT CGCGT CACGG CTAT TGG R9
                                         (SEQ ID NO: 13)
CATTT GCGGT GGTAA TCGC AGG R10
                                         (SEQ ID NO: 14)
GATCG GATCG GGTCG CGTC GGG Human CD147:
L147
                                         (SEQ ID NO: 15)
TTTCC TGCGC TGAAT CGGG TGG R147
                                         (SEQ ID NO: 16)
GGCTC CTGTC TGTGC CTGA CGG
```

EXAMPLE II

Cas9 and sgRNA Plasmid Construction

The U6 promoter and sgRNA backbone sequence were synthesized as described {Mali:2013eu} (IDT) and cloned using isothermal assembly {Gibson:2009bc} into a minimal plasmid backbone containing the Ampicillin resistance gene and pBR322 ori PCR amplified from pUC19 using primers 5' CTTTCTTGTACAAAGTTGGCATTA ttagacgtcaggtggcactttttc 3' (SEQ ID NO:17) and 5' CCTTTAAAGCCTGCTTTTTTGTACA GTTTGCGTATTGGGCGCTCTTC 3' (SEQ ID NO:18). Various sgRNA sequences were cloned into this vector using isothermal assembly. The overlapping segments for isothermal assembly are underlined. All primers were from IDT; all PCR reactions were done with the KAPA HiFi HotStart PCR kit. Plasmids were maintained in either TOP10 or Stbl3 bacteria (Invitrogen).

A human codon-optimzed Cas9 nuclease gene {Mali:2013eu} was PCR amplified using primers 5' GCCACCATGGACAAGAAGTACTCC 3' (SEQ ID NO:19) and 5' TCACACCTTCCTCTTCTTCTTGGG 3' (SEQ ID NO:20) and cloned using isothermal assembly between an EF1α promoter and a bGH polyadenylation sequence on a pCDNA3 plasmid backbone. The EF1α promoter was PCR amplified from pEGIP (Addgene #26777) using primers 5' CCGAAAAGTGCCACCTGACGTCGACGGA tgaaaggagtgGGAATTggc 3' (SEQ ID NO:21) and 5' GGAGTACTTCTTGTCCATGGTGGC GGCC AACTAGCCAGCTTGGGTCTCCC 3' (SEQ ID NO:22). The bGH polyadenylation sequence was PCR amplified from pST1374 (Addgene #13426){Maeder:2009bp} using primers 5' GCTGACCCCAAGAAGAAGAGGAAGGTGTGA CATCACCATTGAGTTTAAACCCGC 3' (SEQ ID NO:23) and 5' CCAAGCTCTAGCTAGAGGTCGACG GTAT C GAGCCCCAGCTGGTTC 3' (SEQ ID NO:24). The plasmid backbone was PCR amplified from pCDNA3 (Invitrogen) using primers 5' ATACCGTCGACCTCTAGCTAG 3' (SEQ ID NO:25) and 5' TCCGTCGACGTCAGGTGG 3' (SEQ ID NO:26).

EXAMPLE III

Targeting Plasmid Construction

The mouse Thy1 targeting vector with homology around the sgRNA sites (Outside) was cloned using isothermal assembly. Exons 2 and 3 of mouse Thy1 were PCR amplified from C57BL/6J genomic DNA (Jackson Laboratories) using primers 5' TGGTGGTGGTTGTGGTACACACC 3' (SEQ ID NO:27) and 5' AATAGGGAGGGCCGGGGTACC 3' (SEQ ID NO:28). The upstream human Thy1 homology arm was PCR amplified from PGP1 iPSC genomic DNA using primers 5' AC CCTTCCCCTCCTAGATCCCAAGCC 3' (SEQ ID NO:29) and 5' GATTAAAGGTGTGTACCACAACCACCACCA CTTTTCTGAGACTGTGAGGGAG 3' (SEQ ID NO:30). The downstream human Thy1 homology arm was PCR amplified from PGP1 human iPSC genomic DNA using primers 5' AGACTCTGGGGTACCCCGGCCCTCCCTATT CCCAGGGGCTAATGACTGC 3' (SEQ ID NO:31) and 5' GCACCTCCAGCCATCACAGC 3' (SEQ ID NO:32). The plasmid backbone was PCR amplified from pUC19 using primers 5' CCAGGAAGGGGCTGTGATGGCTGGAGGTGC ttagacgtcaggtggcactttttc 3' (SEQ ID NO:33) and 5' GGGCTTGGGATCTAGGAGGGGAAGG GTTTGCGTATTGGGCGCTCTTC 3' (SEQ ID NO:34).

A linear version of the mouse Thy1 targeting vector was PCR amplified from the original Outside targeting vector using primers 5' AC CCTTCCCCTCCTAGATCCCAAGCC 3' (SEQ ID NO:35) and 5' GCACCTCCAGCCATCACAGC 3' (SEQ ID NO:36). PCR products were cleaned with the Qiaquick PCR Purification kit (Qiagen).

Versions of the mouse Thy1 targeting vector with shorter homology arms were cloned from the original Outside Thy1 targeting vector plasmid using isothermal assembly using combinations of the following three forward and three reverse PCR primers. Forward primers determining the length of the upstream homology arm:

1550 bp, L: 5' ACCCTTCCCCTCCTAGATCCCAAGCC 3' (SEQ ID NO:37);
821 bp, M: 5' AAGATTCAGAGAGATTCATTCATTCATTCACAA 3' (SEQ ID NO:38);
100 bp, S: 5' CCTGCTAACAGGTACCCGGCATG 3' (SEQ ID NO:39).

Reverse primers determining the length of the downstream homology arm:
2466 bp, L: 5' GCACCTCCAGCCATCACAGC 3' (SEQ ID NO:40);
797 bp, M: 5' CAGCATCTTGCTAAGGGGTTGTCAG 3' (SEQ ID NO:41);
94 bp, S: 5' GTCAGCAGACATGGGATGTTCGTTT 3' (SEQ ID NO:42).

The plasmid backbone was PCR amplified from pUC19 using the following three forward and reverse primers with complementary overhangs to the upstream and downstream Thy1 homology arms.
Upstream overhangs:
1550 bp: 5' GGGCTTGGGATCTAGGAGGGGAAGG GTTTGCGTATTGGGCGCTCTTC 3' (SEQ ID NO:43);
821 bp: 5' TGAATGAATGAATGAATCTCTCTGAATCTT GTTTGCGTATTGGGCGCTCTT C 3' (SEQ ID NO:44);
100 bp: 5' TCCTGCCCCATGCCGGGTACCTGTTAGCAG GTTTGCGTATTGGGCGCTCTTC 3' (SEQ ID NO:45).

Downstream overhangs:
2466 bp: 5' CCAGGAAGGGGCTGTGATGGCTGGAGGTGC ttagacgtcaggtggcactttttc 3' (SEQ ID NO:46);
797 bp: 5' GGAGGCTGACAACCCCTTAGCAAGATGCTG ttagacgtcaggtggcactttttc 3' (SEQ ID NO:47);
94 bp: 5' CAAATAAACGAACATCCCATGTCTGCTGAC ttagacgtcaggtggcactttttc 3' (SEQ ID NO:48).

A version of the mouse Thy1 targeting vector with longer homology arms (XX) was cloned using isothermal assembly. The original Outside Thy1 targeting vector plasmid was PCR amplified using primers 5' CCTTCCCCTCCTAGATCCAAGCC 3' (SEQ ID NO:49) and 5' GCACCTCCAGCCATCACAGC 3' (SEQ ID NO:50). An extra 3 kb of the Thy1 upstream homology arm was PCR amplified from PGP1 genomic DNA using primers 5' TCTTGTTTGAGATGTTGTGCGGG 3' (SEQ ID NO:51) and 5' CTGGTTTCAGCACTCCGATCCTATC 3' (SEQ ID NO:52). An extra 2.4 kb of the Thy1 downstream homology arm was PCR amplified from PGP1 genomic DNA using primers 5' TGTGGCTCTGCACCAGGAAG 3' (SEQ ID NO:53) and 5' CCTCTCCCTTTTCCCTGGTTTTG 3' (SEQ ID NO:54). The plasmid backbone with complementary overhangs was PCR amplified from pUC19 using primers 5' TACTCTGCAAAACCAGGGAAAAGGGAGAGG ttagacgtcaggtggcactttttc 3' (SEQ ID NO:55) and 5' CTGTGGATAGGATCGGAGTGCTGAAACCAG GTTTGCGTATTGGGCGCTCTTC 3' (SEQ ID NO:56).

The mouse Thy1 targeting vector with homology around each sgRNA site (Intact) was cloned using isothermal assembly. A shorter fragment of mouse Thy1 exons 2 and 3 was PCR amplified from the original Outside Thy1 targeting vector plasmid using primers 5' ATCTCTCCACTTCAGGTGGGTGGGAGGCCCCTGT GGTCTGTGTCTCCCCAAATT 3' (SEQ ID NO:57) and 5' CAGGTGGACAGGAGGACAGATTCCAGAGGC TTGGTTTTATTGTGCAGTTTTCTTTC 3' (SEQ ID NO:58). An extended fragment of the upstream homology arm within the sgRNA sites was PCR amplified from PGP1 genomic DNA using primers 5' GGCTTCCTTCCCTCCAGAG 3' (SEQ ID NO:59) and 5' ACAGGGGCCTCCCACCC 3' (SEQ ID NO:60). An extended fragment of the downstream homology arm within the sgRNA sites was PCR amplified from PGP1 genomic DNA using primers 5' CAAGCCTCTGGAATCTGTCCTC 3' (SEQ ID NO:61) and 5' GCCCAGTGTGCAGTCATTAGC 3' (SEQ ID NO:62). The plasmid backbone with the remaining upstream and downstream homology arm fragments was PCR amplified from the original Outside Thy1 targeting vector using primers 5' CTTTTCTGAGACTGTGAGGGAG 3' (SEQ ID NO:63) and 5' TACCCCAGGGGCTAATGACTGCAC 3' (SEQ ID NO:64).

The mouse Thy1 targeting vector with homology around each disrupted sgRNA site (Disrupted) was cloned using isothermal assembly. To delete one nucleotide from each of the sgRNA sites, two sections were PCR amplified from the Intact Thy1 targeting vector plasmid with primers 5' ACAGTCTCAGAAAACGCAGGTGACAAAG 3' (SEQ ID NO:65) and 5' CATTAGCCCCTGGGTAGCGTTGCTACTAAG 3' (SEQ ID NO:66) and then 5' TTGTCACCTGCGTTTTCTGAGACTGTGAG 3' (SEQ ID NO:67) and 5' CTTAGTAGCAACGCTACCCAGGGGCTAATG 3' (SEQ ID NO:68).

The mCherry Thy1 targeting vector was cloned using isothermal assembly. The mCherry transgene was PCR amplified from a plasmid construct containing mCherry under the control of a pGK promoter with a bGH polyadenylation sequence using primers 5' GAGAATACCAGCAGTTCACCCATCCAGTACGAAATTCTACCGGGTA GGGGAG 3' (SEQ ID NO:69) and 5' CCCAGTGTGCAGTCATTAGCCCCTGGGGTA CGACGGCCAGTGAATTGTAATACG 3' (SEQ ID NO:70). The upstream homology arm was PCR amplified from PGP1 genomic DNA using primers 5' AC CCTTCCCCTCCTAGATCCCAAGCC 3' (SEQ ID NO:71) and 5' GTACTGGATGGGTGAACTGCTGGTATTC 3' (SEQ ID NO:72). The downstream homology arm was PCR amplified from PGP1 genomic DNA using primers 5' TACCCCAGGGGCTAATGACTGCAC 3' (SEQ ID NO:73) and 5' GCACCTCCAGCCATCACAGC 3' (SEQ ID NO:74). The plasmid backbone was PCR amplified from pUC19 using primers 5' CCAGGAAGGGGCTGTGATGGCTGGAGGTGC ttagacgtcaggtggcactttc 3' (SEQ ID NO:75) and 5' GGGCTTGGGATCTAGGAGGGGAAGGGTTTGCGTATTG GGCGCTCTTC 3' (SEQ ID NO:76).

The mouse CD147 targeting vector was cloned using isothermal assembly. Exons 2-7 of mouse CD147 were PCR amplified from C57BL/6J genomic DNA (Jackson Laboratories) using primers 5' GAAGTCGAGGTTCCAAGGTCACAGTGAG GGGGCCCTGGCCACCC CTTGCAGGTTCTCCATAGTCCACAG 3' (SEQ ID NO:77) and 5' CAACAACCCCTCCTGTATATGACCT 3' (SEQ ID NO:78). The upstream homology arm was PCR amplified from PGP1 genomic DNA using primers 5' ACACACTTTCAACCTCCAAGAGACG 3' (SEQ ID NO:79) and 5' CTCACTGTGACCTTGGAACCTCG 3' (SEQ ID NO:80). The downstream homology arm was PCR amplified from PGP1 genomic DNA using primers 5' TGTTGAGGTCATATACAGGAGGGGTTGTTG CCTGACGGGGTTGGGTTTTCC 3' (SEQ ID NO:81) and 5' AA GGGAGCCCTGAGGCCTTTTCC 3' (SEQ ID NO:82).

The plasmid backbone with complementary overhangs was PCR amplified from pUC19 using primers 5' TCAGGAAAAGGCCTCAGGGCTCCC ttagacgtcaggtggcactttc 3' (SEQ ID NO:83) and 5' CGTCTCTTGGAGGTTGAAAGTGTGT GTTTGCGTATTGGGCGCTCTTC 3' (SEQ ID NO:84).

EXAMPLE IV

TALEN Assembly

TALE pairs (16.5mer) targeting the human Thy1 gene were assembled using Iterative Capped Assembly{Briggs:2012di}. TALE pair targeting over the L3 sgRNA site: Left: 5' T ACCAGCAGTTCACCCAT 3' (SEQ ID NO:85); Right: 5' T CTTTGTCTCACGGGTCA 3' (SEQ ID NO:86). TALEN pair targeting over the R1 sgRNA site: Left: 5' T CTCCCCAACCACTTAGT 3' (SEQ ID NO:87); Right: 5' T GTGCAGTCATTAGCCCC 3' (SEQ ID NO:88). TALE were cloned onto FokI heterodimer nuclease domains using isothermal assembly. Assembled TALE were PCR amplified using primers 5' GGCCGCCACCATGGATTATAAGGAC 3' (SEQ ID NO:89) and 5' GGAACCTGCCACTCGATGTG 3' (SEQ ID NO:90). The FokI heterodimer nuclease domains KKR and ELD with the Sharkey mutations {Doyon:2010dm, Guo:2010df} were derived from pMG10 (Addgene #31238){Sollu:2010gh} using the QuikChange Lightning Site-Directed Mutagenesis Kit (Stratagene). The KKR-Sharkey FokI domain was PCR amplified using primers 5' GACATCACATCGAGTGGCAGGTTCC CAGCTGGTGAAGTCCGAGC 3' (SEQ ID NO:91) and 5' CAACTAGAAGGCACAGTCGAGGC TGATCAGCG GGGTTA GAAATTGATTTCACCATTGTTGAAC 3' (SEQ ID NO:92). The ELD-Sharkey FokI domain was PCR amplified using primers 5' GACATCACATCGAGTGGCAGGTTCC CAACTAGTCAAAAGTGAACTGGAGG 3' (SEQ ID NO:93) and 5' CAACTAGAAGGCACAGTCGAGGC TGATCAGCG CCCTTAAAAGTTTATCTCGCCG 3' (SEQ ID NO:94). Each TALE and FokI heterodimer domain was cloned into a plasmid backbone containing an EF1α promoter and bGH polyadenylation sequence; this was amplified from the Cas9 expression vector described above using primers 5' GCCTCGACTGTGCCTTCTAGTTG 3' (SEQ ID NO:95) and 5' CTTATAA TCCATGGTGGCGGCC 3' (SEQ ID NO:96).

EXAMPLE V iPSC Culture and Transfection

Verified human iPSC from Personal Genome Project donors PGP1 and PGP4 {Ball:2012kr} were obtained through Coriell. Cell lines were maintained on Matrigel-coated plates (BD) and grown in mTesr1 (Stem Cell Technologies) according to manufacturer's instructions. 10 µM of the Rock inhibitor Y-27632 (Millipore) was added to the culture before, during, and after passaging with Accutase (Millipore). Pluripotency of iPSC cultures was verified by TRA-1/60 FACS staining (BD).

All plasmids were purified using the Qiagen Endo-free Plasmid Maxiprep kit. Plasmids were nucleofected into iPSC cells using the Lonza 4D-Nucleofector X unit (Buffer P3, Program CB-150) according to manufacturer's instructions. For each 20 µl nucleofection reaction, 0.2-0.5×10$^6$ iPSC were transfected with up to 4 µg of plasmid DNA. Post-nucleofection, iPSC were plated onto 24- and 96-well Matrigel-coated plates containing mTesr1 media plus 10 µM Y-27632.

For CRISPR-based nucleofections with a targeting vector (See FIGS. 1(a)-(d) and FIGS. 3(a)-(c) to FIGS. 8(a)-(c), 2

μg of targeting vector plasmid, 0.5 μg of Cas9 plasmid, and 1.5 μg of total sgRNA plasmid were used. When two sgRNAs were used, 0.75 μg of each plasmid was combined. When no sgRNAs were used, 1.5 μg of pUC19 was used instead.

For CRISPR-based nucleofections without a targeting vector (See FIG. 2(a)-(e)), 2 μg of total plasmid was used: 0.5 μg of Cas9 plasmid with 0.75 μg of each sgRNA plasmid or 0.75 μg of pUC19.

Figure 5:
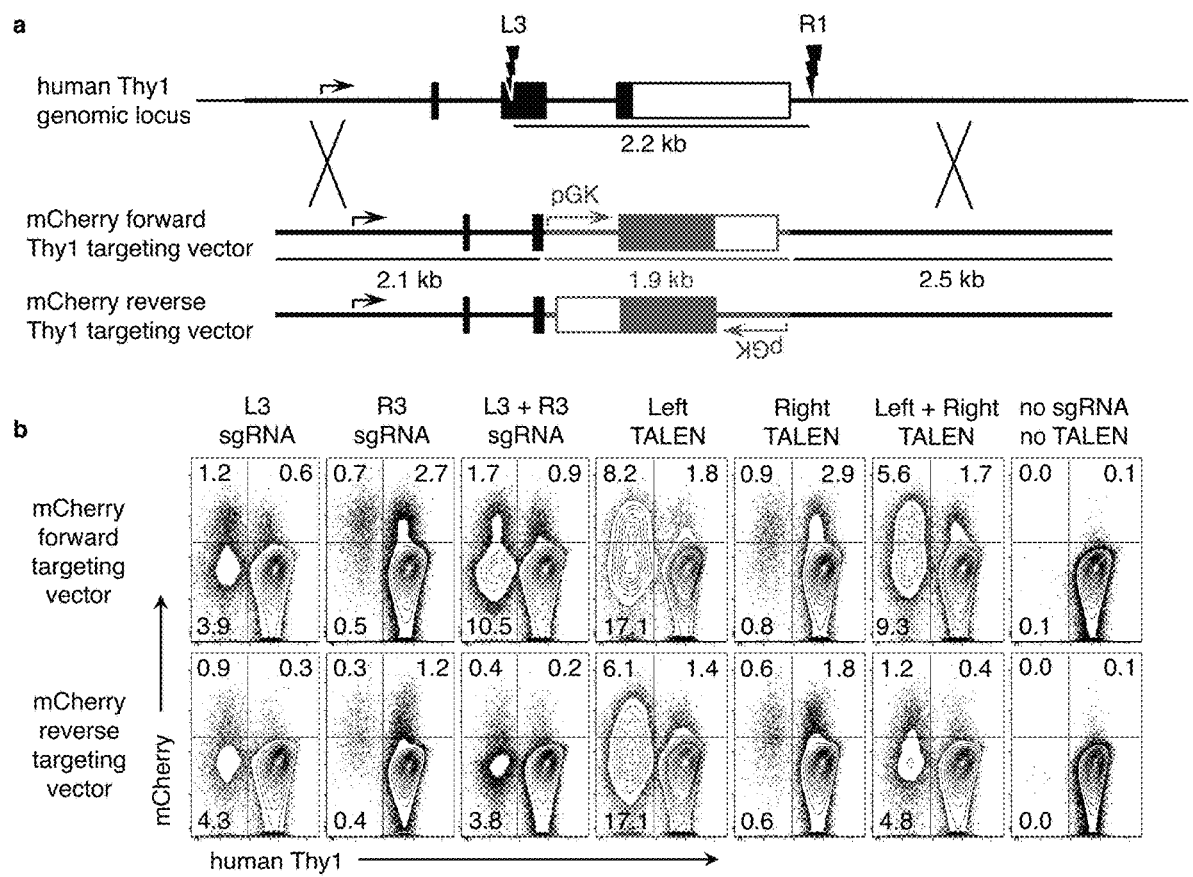
FIG. 5(a)-(b). Targeted gene replacement in either gene orientation with Crispr or TALEN.
Figure 6:
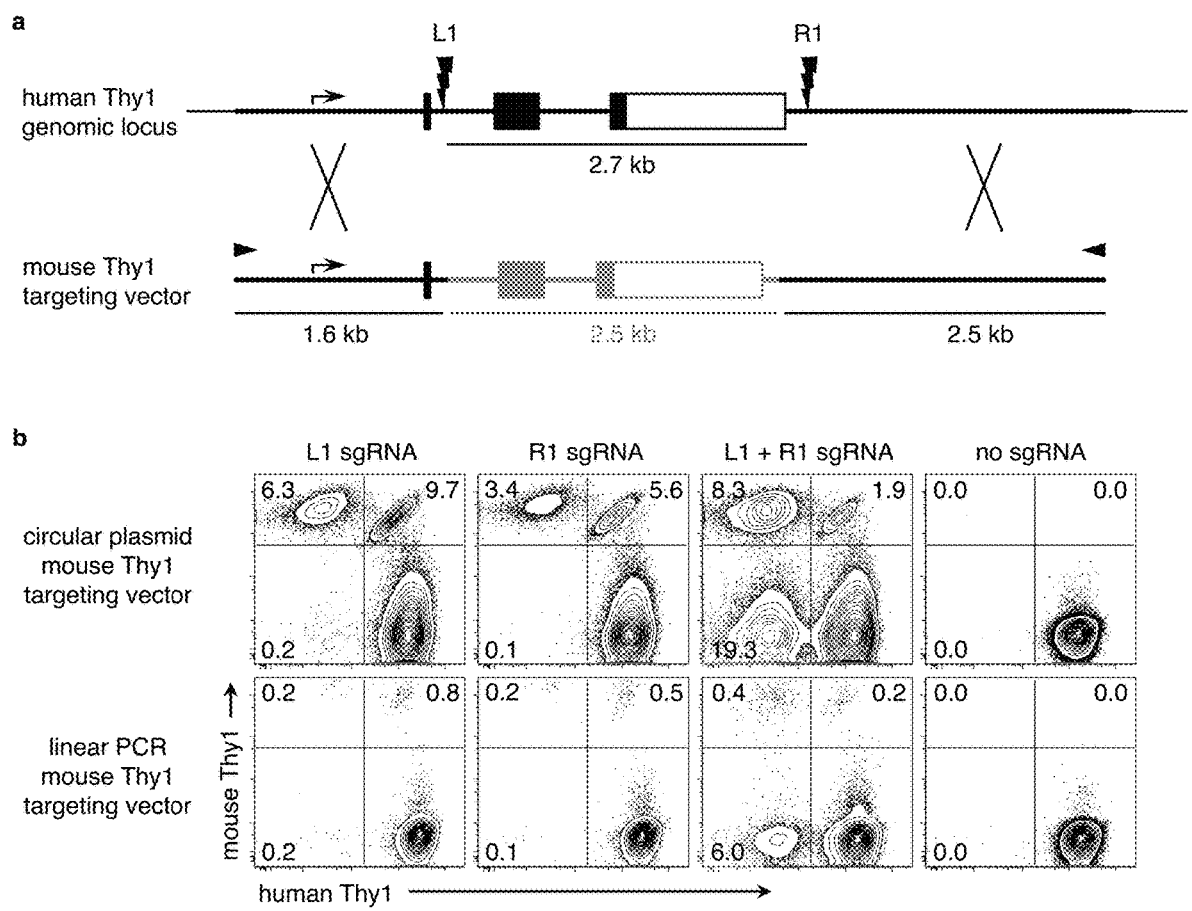
FIG. 6(a)-(b). Targeted gene replacement using circular or linear targeting vectors.

For TALEN-based nucleofections with a targeting vector (See FIG. 5(a)-(b)), 2 μg of targeting vector plasmid plus 2 μg total of TALEN plasmid was used. For one dsDNA break using one TALEN pair, 1 μg of each TALEN-expressing heterodimer plasmid was used. For two dsDNA breaks using two TALEN pairs, 0.5 μg of each TALEN-expressing heterodimer plasmid was used.

EXAMPLE VI

FACS Staining iPSC were dissociated using TrypLE Express (Invitrogen) and washed in FACS buffer: PBS (Invitrogen)+0.2% bovine serum albumin (Sigma). Cells were stained in FACS buffer plus 10% fetal calf serum for 30 min at 4° C. The following antibodies were purchased from eBioscience: Anti-human Thy1 APC (eBio5E10), anti-mouse Thy1.2 PE (30-H12), anti-human CD147 APC (8D12), anti-mouse CD147 PE (RL73), isotype control mouse IgG1 κ APC (P3.6.2.8.1), isotype control mouse IgG2b PE (eBMG2b). Cells were washed twice in FACS buffer, and then resuspended in FACS buffer with the viability dye SYTOX Blue (Invitrogen). Samples were collected on a BD LSRFortessa flow cytometer with a High Throughput Sampler (HTS) and analyzed using FlowJo software (Tree Star).

For the constant viable cell counts shown in FIG. 8(a)-(c), each sample was grown in one well of a 96-well plate. Each well was dissociated with 50 μl TrypLE. Then, 150 μl of FACS buffer containing the viability dye ToPro3 (Invitrogen) was added. The HTS was used to analyze 100 μl from each well at a constant rate of 1 μl/s with mixing.

EXAMPLE VII

Single-Cell iPSC FACS Sorting

For FACS sorting, iPSC were sorted one cell/well into 96-well plates containing feeder cells. 96-well flat-bottom tissue culture plates were coated with gelatin (Millipore) and cultured with irradiated CF-1 mouse embryonic fibroblasts ($10^6$ MEFs per plate; Global Stem) the night before. Before sorting, media in the plates was changed to hES cell maintenance media {Lerou:2008dt} with 100 ng/ml bFGF (Millipore), SMC4 inhibitors {Valamehr:2012dd} (BioVision), and 5 μg/ml fibronectin (Sigma).

For at least 2 hours before FACS sorting, iPSC were pre-treated with mTesr1 containing SMC4 inhibitors. Cells were dissociated with Accutase, and stained as described above. iPSC were sorted using a BD FACS Aria into the MEF-coated 96-well plates. Established iPSC colonies were then mechanically passaged onto new MEF-coated wells.

EXAMPLE VIII

PCR Genotyping

Genomic DNA from sorted iPSC clones was purified from the 96-well plates {RamirezSolis:1992vu}. Each clone was genotyped using four sets of PCR primers (See FIG. 1(a)-(d)) using the KAPA HiFi HotStart polymerase and run on a 0.8% agarose gel.

Reaction 1: 5' AGGGACTTAGATGACTGCCATAGCC 3' (SEQ ID NO:97) and 5' ATGTTGGCAGTAAGCATGTTGTTCC 3' (SEQ ID NO:98). Wild type Thy1 (+) or inverted allele (i): 3129 bp; Targeted mouse Thy1 allele (m): 2904 bp; Excised allele (Δ): 387 bp.

Reaction 2: 5' AGGGACTTAGATGACTGCCATAGCC 3' (SEQ ID NO:99), 5' CTCACCTCTGAGCACTGTGACGTTC 3' (SEQ ID NO:100), and 5' ACTGAAGTTCTGGGTCCCAACAATG 3' (SEQ ID NO:101). Wild type allele (+): 993 bp; Targeted mouse allele (m): 490 bp; excised (Δ) or inverted (i) allele: no PCR product.

Reaction 3: 5' ATGAATACAGACTGCACCTCCCCAG 3' (SEQ ID NO:102), 5' CTCACCTCTGAGCACTGTGACGTTC 3' (SEQ ID NO:103), and 5' CCATCAATCTACTGAAGTTCTGGGTCCCAACAATG 3' (SEQ ID NO:104). Wild type allele (+): 2393 bp; Targeted mouse allele (m): 1891 bp; excised (Δ) or inverted (i) allele: no PCR product.

Reaction 4: 5' TGAAGTGAAACCCTAAAGGGGGAAG 3' (SEQ ID NO:105), 5' AAACCACACACTTCAACCTGGATGG 3' (SEQ ID NO:106), and 5' GTTTGGCCCAAGTTTCTAAGGGAGG 3' (SEQ ID NO:107). Wild type allele (+): 3064 bp; Targeted mouse allele (m): 2707; excised (Δ) or inverted (i) allele: no PCR product.

Genomic DNA from sorted iPSC clones was PCR amplified using the primers in genotyping Reaction 1, which span outside the sgRNA nuclease sites. Different size PCR products were separated using agarose gel extraction (Qiagen). PCR products were Sanger sequenced (Genewiz) using the same two primers. Single and double peaks were analyzed from the Sanger trace file and deconvoluted to ascertain the biallelic sequences of each clone.

EXAMPLE IX

Aspects of the present disclosure are directed to improving the low frequency of homologous recombination (HR) ($10^{-3}$-$10^{-7}$) which may limit targeted gene replacements even when using antibiotic selection markers. See {Deng:1992w1}. Aspects of the present disclosure envision the use of custom-engineered nuclease systems, such as zinc finger nucleases (ZFN){Urnov:2010bz}, transcription activator-like effector nucleases (TALEN){Joung:2012de}, or CRISPR/Cas9 nucleases {Mali:2013eu} for efficient genome modification, such as the excision and replacement of long nucleic acid sequences, such as long gene sequences. Aspects of the present disclosure envision use of cell types which may be resistant to gene editing using conventional methods.

Aspects of the present disclosure envision use of one or more dsDNA breaks at specific target sites, wherein the NHEJ repair pathway {Chapman:2012kd} can then mutate and disrupt genes {Urnov:2010bz, Mali:2013eu}. Aspects of the present disclosure envision two dsDNA breaks which can excise the intervening portion of the genome {Lee:2010if} or generate translocations {Piganeau:2013cp}. Aspects of the present disclosure envision the use of HR using an ssODN {Chen:2011dz, Yang:2013jr} or plasmid targeting vector {Yang:2013jr, Mali:2013eu} to introduce mutations or transgenes {Moehle:2007gw, Hockemeyer:2009js}. Aspects of the present disclosure envision methods described herein for improving the efficiency of gene insertion of larger insertions which may be inefficient. {Moehle: 2007gw, Urnov:2010bz}.

Aspects of the present disclosure envision generating multi-kilobase targeted gene replacements using the methods described herein and microhomology-mediated end joining (MMEJ) between the short single-stranded overhangs which may result from ZFN cleavage {Orlando: 2010cs, Cristea:2013cf, Maresca:2013dr}. Aspects of the present disclosure envision improving efficiency of HR crossovers between the flanking homology arms by generating a dsDNA break at each homology arm. Further envisioned is the use of multiple cut sites at each homology arm to improve efficiency of large nucleic acid insertion.

EXAMPLE X

Optimizing Target Vector Design

Aspects of the present disclosure relate to optimizing targeting vector design for large nucleic acid replacement. According to one exemplary aspect, the 2.7 kb human Thy1 gene (hThy1) was replaced with its mouse homologue (mThy1) in human iPSC derived from Personal Genome Project (PGP) donors. Human Thy1 (CD90) is advantageous to demonstrate an example of large gene replacement using the methods described herein because it is expressed on the surface of human iPSC, it is not essential for cell survival in vitro, and species-specific staining antibodies are available. It is to be understood that this example is exemplary only and is not intended to limit the scope of the present disclosure to excision of human Thy1 and replacement with mouse Thy1.

Two single guide RNAs (sgRNA) were designed that target human Thy1 within intron 1 or after the polyadenylation sequence. The mThy1 targeting vector plasmid contained exons 2 and 3 of mouse Thy1 flanked by human Thy1 homology arms outside of the cut sites (FIG. 1a). When both dsDNA breaks were made, 6.7% of iPSC became mThy1$^+$hThy1$^-$ without selection (FIG. 1b). PCR genotyping of single cell FACS-sorted mThy1$^+$hThy1$^-$ iPSC clones revealed a mixture of homozygous targeted replacement (m/m; 4.7%) and replacement of one human allele with excision of the other (m/Δ; 2%) (FIG. 1(c)-(d)). Furthermore, 1.6% of cells were mThy1$^+$hThy1$^+$ double positive (m/+; heterozygous targeted replacement).

Finally, 16.2% of cells were mThy1$^-$hThy1$^-$ double negative: PCR and Sanger sequencing revealed a mixture of homozygous excision (Δ/Δ) and heterozygous inversion and excision (i/Δ) between the sgRNA sites (FIG. 1(a)-(d)). While a few indels and inserted bases were observed at the excision and inversion sites, the largest indel was only 15 bp, and most alleles were re-joined exactly between the cut sites (FIG. 3(a)-(c)). Previous reports generating two dsDNA breaks with ZFN or TALEN observed indels in most excision and inversion alleles, up to 200 bp {Lee:2010if, Lee: 2012fx, Piganeau:2013cp}. In contrast to the 5' overhangs produced by ZFN and TALEN, Cas9 nucleases produce blunt-end dsDNA breaks {Jinek:2012hm}, which may contribute to the increased fidelity of re-joining, which was also seen for shorter 19 bp {Mali:2013eu} and 118 bp {Cong: 2013fe} Cas9-mediated excisions.

When only a single sgRNA was used, mThy1 homozygous replacement occurred in >2% of cells (mThy1$^+$hThy1$^-$; m/m) and heterozygous replacement occurred in 4-6% of cells (mThy1$^+$hThy1$^+$; m/+). Very few mThy1$^-$hThy1$^-$ double negative cells and no excised hThy1 alleles (A) were observed (FIG. 1(a)-(d)). A similar pattern of results occurred when replacing the 9.8 kb human CD147 gene with its mouse homologue or replacing hThy1 with a fluorescent reporter (FIG. 4(a)-(b) and FIG. 5(a)-(b)).

EXAMPLE XI

Determining the Effect of Homology Length on Targeted Gene Replacements in Human iPSC Conventional gene targeting vectors are typically transfected as linearized plasmids. With ZFN, circular plasmid targeting constructs produced higher rates of HR-mediated gene insertion than linearized plasmids, although linear constructs were more effective at MMEJ-mediated gene insertion {Orlando:2010cs, Cristea:2013cf}. A linearized mThy1 targeting vector produced far less gene targeting compared to the circular plasmid (FIG. (a)-(b)), which may be due to the reduced nucleofection efficiency of linearized plasmids or increased degradation{Cristea:2013cf}.

Figure 7:
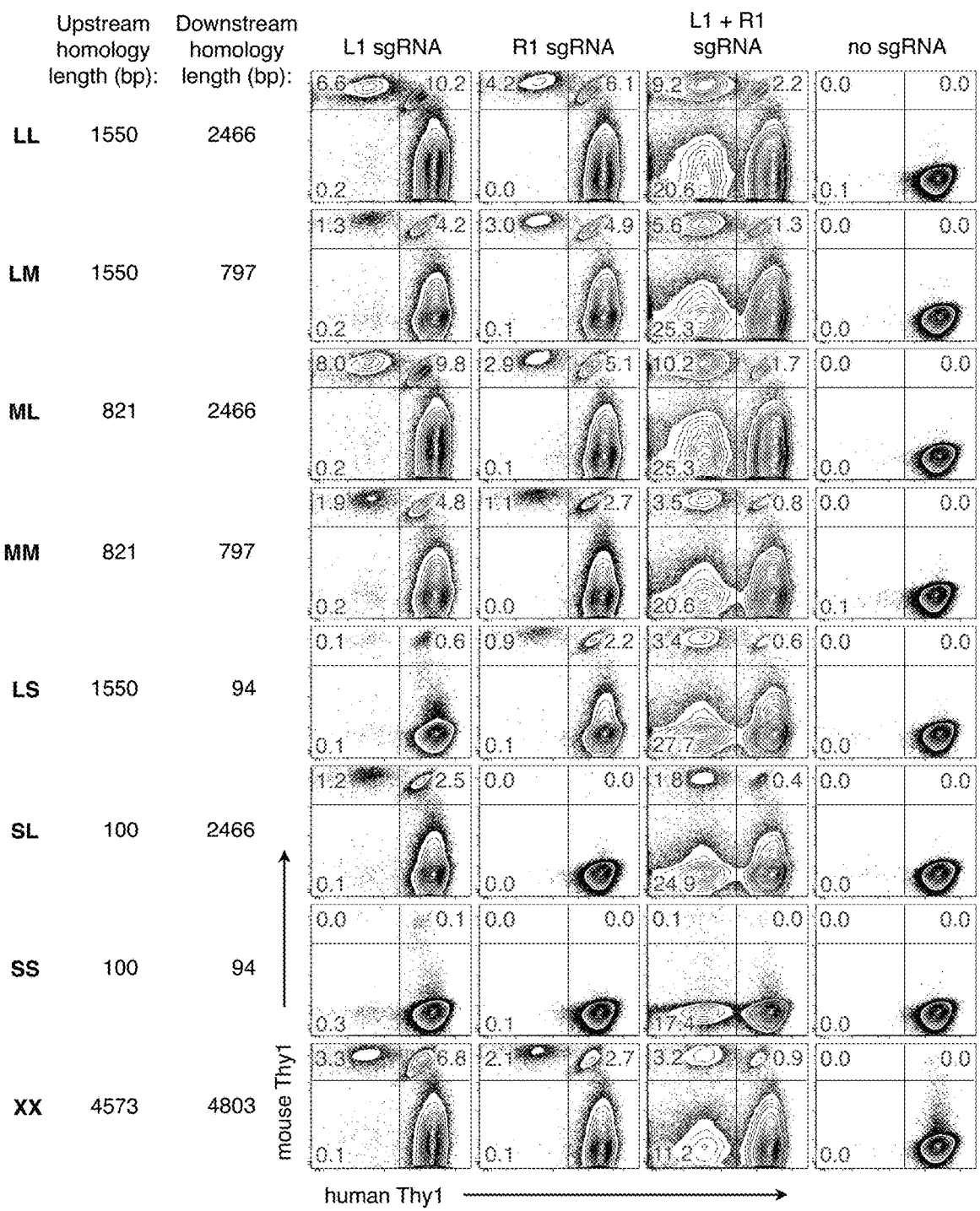
FIG. 7(a)-(b). Effect of homology arm length on recombination efficiency. Versions of the mouse Thy1 targeting vector plasmid (FIG. 1a) were constructed with homology arms of various lengths, but still containing the 2.5 kb sequence encompassing mouse Thy1 exons 2 and 3. The length of the upstream and downstream homology arms in each vector is indicated. Each mouse Thy1 targeting vector was nucleofected into FIG. 7(a) PGP1 or FIG. 7(b) PGP4 iPSC along with plasmids encoding the Cas9 nuclease and L1, R1, both, or no sgRNAs. Ten days later, cells were analyzed by flow cytometry for expression of the mouse and human Thy1 genes. The frequency of cells in each fluorescence quadrant is indicated. Results are representative of two independent experiments.
Figure 7:
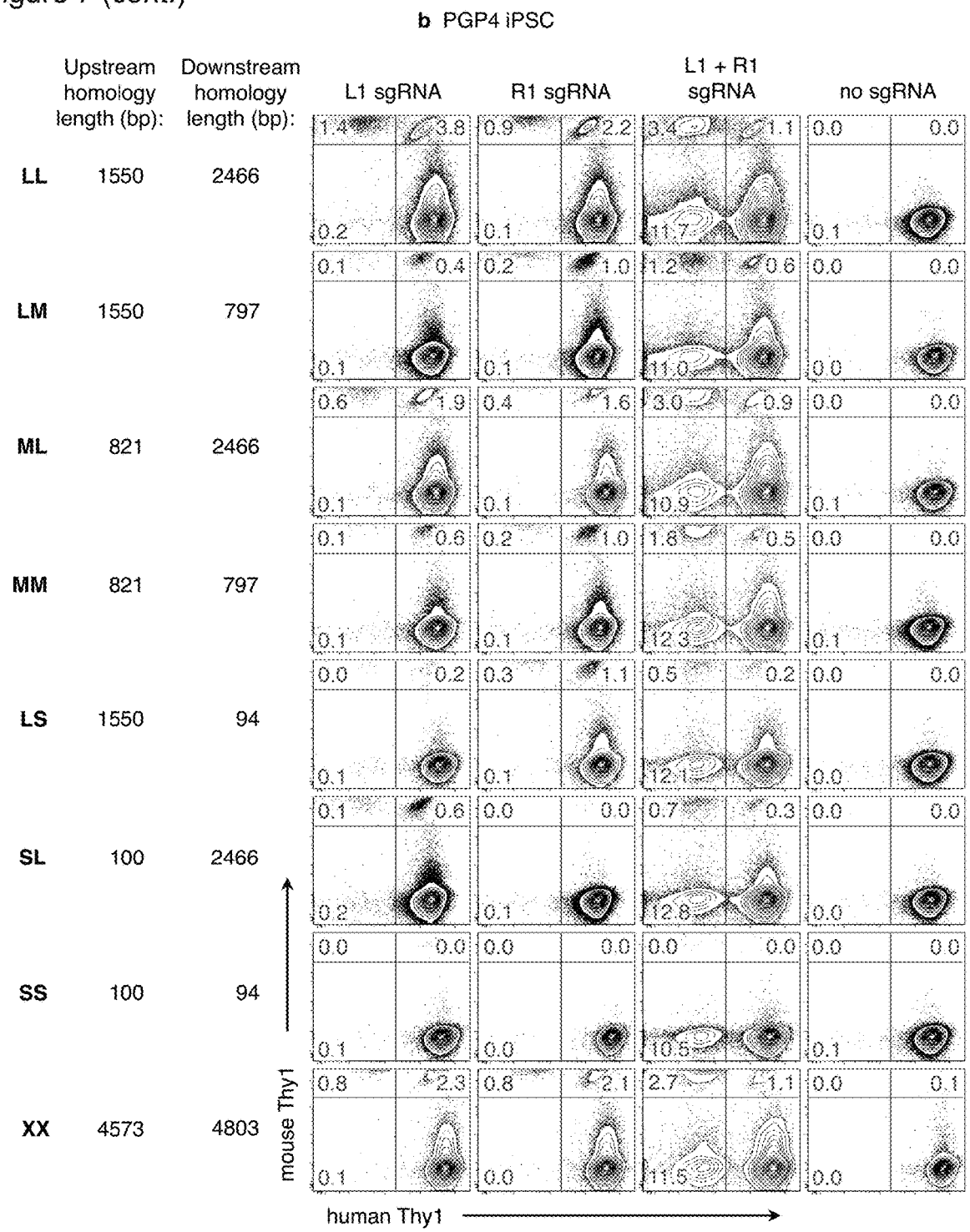

For conventional HR-mediated gene targeting, targeting frequency increased with homology arm length up to ~14 kb {Deng:1992w1}, although additional homology arm length (up to ~70 kb) using bacterial artificial chromosomes can improve weak or non-isogenic targeting vectors {Valenzuela:2003ez}. However, introducing a dsDNA break reduces the necessary homology arm length to ~0.2-0.8 kb for transgene insertions into a single cut site {Elliott:1998uz, Moehle:2007gw, Hockemeyer:2009js, Orlando:2010cs, Beumer:2013cb}. To examine the effect of homology length on targeted gene replacements in human iPSC, versions of the mThy1 targeting vector were constructed with various length homology arms (FIG. 7(a)). In addition to the ~2 kb homology arms from the original targeting vector (long, L), shorter lengths of ~800 bp (medium, M) or ~100 bp (short, S) were chosen, as these lengths are often used for HR-mediated gene insertion {Moehle:2007gw, Hockemeyer: 2009js} or ssODN correction {Chen:2011dz, Yang:2013jr}. Longer homology arms of ~5 kb (extra-long, X) were also tested. With two dsDNA breaks, targeting frequencies were highest with ~2 kb homology arms (LL and ML), and generally declined with less homology, although frequencies >1% were achieved down to ~1.5 kb total homology (MM, LS, and SL). Extra-long homology arms did not improve gene targeting efficiency (XX versus LL).

When only one dsDNA break was used, homology length was most important on the arm opposite the cut site. The LM and LS vectors showed higher gene targeting with the Right sgRNA than the Left; the ML and SL vectors showed higher gene targeting with the Left sgRNA than the Right (FIG. 7(a)). The same pattern of results was observed in PGP4 iPSC, even though the targeting efficiencies were lower (FIG. 7(b)). These results are consistent with a model of Synthesis-Dependent Strand Annealing {Moehle:2007gw, Urnov:2010bz, Chapman:2012kd}: the resected chromosome outside the dsDNA break anneals to the corresponding sequence in the targeting vector plasmid. The heterologous mouse Thy1 sequence in the targeting vector is incorporated, forming a D-loop, until human sequence on the opposite homology arm is reached. Sufficient length of this homology arm allows for its subsequent homology search and re-annealing to the corresponding part of the chromosome for resolution of the D-loop.

Under this model, the homology arm sequences should extend outside of the dsDNA break sites, with the heterologous replacement sequence present on the inside. Homology arms spanning either side of each cut site did not enhance targeting efficiency in PGP1 or PGP4 iPSC (FIG. 8(a)-(c)).

Since the targeting vector now included intact sgRNA target sites, twice as much iPSC death was observed (FIG. 8(b)), possibly due to an overwhelming number of dsDNA breaks in the cell. When these sgRNA sites were disrupted by a single by deletion, increased cell death was not observed, but targeting efficiency was still reduced compared to the original mThy1 targeting vector. Without wishing to be bound by scientific theory, the results do not suggest a predominant HR mechanism of double Holliday junctions, where both ends of each dsDNA break anneal to corresponding homologous sequences in the targeting vector, forming separate cross-overs {Chapman:2012kd}.

EXAMPLE XII

Determining the Relationship Between the Frequency and Size of Cas9-mediated Deletions in Human iPSC Multi-kilobase deletions have been achieved using ZFN in tumor cell lines, although the deletion frequency generally declines with larger deletion sizes {Lee:2010if, Chen:2011dz}. To delineate the relationship between the frequency and size of Cas9-mediated deletions in human iPSC, two Left and ten Right sgRNAs were designed that target hThy1 at various distances apart (FIG. 2a). Since no targeting vector was used, cells with both hThy1 alleles disrupted became hThy1⁻ (FIG. 2b). Cells nucleofected with only the Left sgRNA were used to determine the background level of hThy1⁻ cells (FIG. 2b, right column) While the frequency of homozygous deletion above the background level tended to be higher for shorter distances—up to 24% for a 2.7 kb deletion and 8% for a 86 kb deletion—other sgRNA sites produced much lower deletion frequencies, which did not always correspond to size (FIG. 2d).

The frequency of monoallelic deletions was determined using a mThy1⁺hThy1⁺ clonal line of iPSC generated as described in FIG. 1(a)-(d). Since the mThy1 allele does not contain the two Left sgRNA sites, only the single remaining hThy1 allele was subject to deletion. While the frequency of heterozygous deletions was occasionally higher than that for homozygous deletions from the same sgRNA pair, they were usually within a few percentage points (FIG. 2(c)-(e)). Without wishing to be bound by scientific theory, varying nuclease activity among sgRNA sites due to differences in the melting temperature, gene expression, or chromatin environment at the target site {Yang:2013jr}, is likely not the cause of observed variations in gene deletion frequency, as neither the L1 or L2 sgRNA consistently produced more deletions when paired with the same Right sgRNA. Pair-specific variables, such as microhomologies between the two dsDNA cut sites, may influence the deletion frequency.

EXAMPLE XIII

Gene Replacement Using Different Nucleases and the Optimal Design for Gene Replacement Vectors According to certain aspects, the design for gene replacement vectors described herein can be used with different nucleases, as they are not particular to which system generates the DNA break. Efficient multi-kilobase gene replacements have been achieved using ZFN, TALEN, and CRISPR nucleases (FIG. 5(a)-(b) and data not shown). Although targeted gene replacements with one cut site were less efficient, use of a single cut site reduces the potential genotypes and off-target mutations formed. Current techniques require that the dsDNA break must be made within 100 bp of the mutation or insertion site, which limits the potentially available sgRNA sites {Elliott:1998uz, Yang:2013jr}. According to certain aspects, large gene replacements can be made using a wider range of nuclease sites, located around the gene or within introns. Additional unique sgRNA sites are useful within the present methods, avoiding conserved coding sequences within a gene family. This facilitates testing of multiple sgRNAs for a particular region (FIG. 2(a)-(e)). According to the methods described herein, flanking homology arms of up to 2 kb improve gene targeting efficiency (FIG. 7(a)-(b)).

According to certain aspects, methods of making targeted gene replacements (as opposed to gene disruptions or insertions) are provided using DNA binding proteins that have nuclease activity, such as ZFN, TALEN, and CRISPR/Cas nucleases for genome editing. According to certain aspects, methods are provided to isolate targeted clones by screening without selection due to the high targeting efficiencies of gene replacement described herein. According to certain aspects, genes could also be replaced with fluorescent proteins so successfully targeted cells could be selected and cloned by FACS. Gene replacements with heterologous sequences will be particularly beneficial for generating "knock-in" animals or disease models in human cell lines. Particular applications include: placing reporter constructs under endogenous promoters; replacing an endogenous gene with a recoded transgene; or comparative genomics across different species.

REFERENCES

The following references are referred to throughout the specification by author name and year of publication and are hereby incorporated by reference in their entireties for all purposes.
1. Deng, C. & Capecchi, M. R. *Mol. Cell. Biol.* 12, 3365-3371 (1992).
2. Urnov, F. D., Rebar, E. J., Holmes, M. C., Zhang, H. S. & Gregory, P. D. *Nat. Rev. Genet.* 11, 636-646 (2010).
3. Joung, J. K. & Sander, J. D. *Nature Reviews Molecular Cell Biology* 14, 49-55 (2012).
4. Mali, P. et al. *Science* 339, 823-826 (2013).
5. Chapman, J. R., Taylor, M. R. G. & Boulton, S. J. *Molecular Cell* 47, 497-510 (2012).
6. Lee, H. J., Kim, E. & Kim, J.-S. *Genome Research* 20, 81-89 (2010).
7. Piganeau, M. et al. *Genome Research* 23, 1182-1193 (2013).
8. Chen, F. et al. *Nature Methods* 8, 753-755 (2011).
9. Yang, L. et al. *Nucleic Acids Research* (2013). doi: 10.1093/nar/gkt555
10. Moehle, E. A. et al. *Proc. Natl. Acad. Sci. U.S.A.* 104, 3055-3060 (2007).
11. Hockemeyer, D. et al. *Nat Biotechnol* 27, 851-857 (2009).
12. Orlando, S. J. et al. *Nucleic Acids Research* 38, e152 (2010).
13. Cristea, S. et al. *Biotechnol. Bioeng.* 110, 871-880 (2013).
14. Maresca, M., Lin, V. G., Guo, N. & Yang, Y. *Genome Research* 23, 539-546 (2013).
15. Lee, H. J., Kweon, J., Kim, E., Kim, S. & Kim, J. S. *Genome Research* 22, 539-548 (2012).
16. Jinek, M. et al. *Science* 337, 816-821 (2012).
17. Cong, L. et al. *Science* 339, 819-823 (2013).
18. Valenzuela, D. M. et al. *Nat Biotechnol* 21, 652-659 (2003).
19. Elliott, B., Richardson, C., Winderbaum, J., Nickoloff, J. A. & Jasin, M. *Mol. Cell. Biol.* 18, 93-101 (1998).
20. Beumer, K. J., Trautman, J. K., Mukherjee, K. & Carroll, D. *G3 Genes|Genomes|Genetics* 3, 657-664 (2013).

The invention claimed is:

1. A method of altering a target nucleic acid in a human cell comprising
introducing into the human cell one or more first foreign nucleic acids encoding two or more guide RNA sequences complementary to DNA at positions defining a nucleic acid sequence of greater than 1000 base pairs, wherein the nucleic acid sequence includes the target nucleic acid,
introducing into the human cell a second foreign nucleic acid encoding a Cas9 protein that binds to the DNA and is guided by the two or more guide RNA sequences,
introducing into the human cell an exogenous nucleic acid sequence of between greater than 1000 base pairs and about 100,000 base pairs in length to be included into the target nucleic acid sequence, wherein the exogenous nucleic acid sequence is flanked by homology arm sequences between about 1500 to about 2500 bases in length complementary to either side of the target nucleic acid to be removed,
wherein the two or more guide RNA sequences and the Cas9 protein are expressed,
wherein the two or more guide RNA sequences and the Cas9 protein co-localize to the DNA and wherein the Cas9 protein creates two or more double stranded breaks to remove the nucleic acid sequence of greater than 1000 base pairs and wherein the exogenous nucleic acid sequence is inserted between the two break points of the DNA by homologous recombination.

2. The method of claim 1 wherein the positions defining a nucleic acid sequence of greater than 1000 base pairs define a nucleic acid sequence of between about 10,000 base pairs and about 100,000 base pairs in length.

3. The method of claim 1 wherein the human cell is a human induced pluripotent stem cell.

4. The method of claim 1 wherein the guide RNA sequence is between about 10 to about 500 nucleotides.

5. The method of claim 1 wherein the guide RNA sequence is between about 20 to about 100 nucleotides.

6. The method of claim 1 wherein the one or more guide RNA sequences is a tracrRNA-crRNA fusion.

7. The method of claim 1 wherein the DNA is genomic DNA, mitochondrial DNA, viral DNA, or exogenous DNA.

8. The method of claim 1 wherein the positions defining a nucleic acid sequence of greater than 1000 base pairs define a nucleic acid sequence of between about 2,000 base pairs and about 100,000 base pairs in length.

9. The method of claim 1 wherein the positions defining a nucleic acid sequence of greater than 1000 base pairs define a nucleic acid sequence of between about 3,000 base pairs and about 100,000 base pairs in length.

10. The method of claim 1 wherein the positions defining a nucleic acid sequence of greater than 1000 base pairs define a nucleic acid sequence of between about 4,000 base pairs and about 100,000 base pairs in length.

11. The method of claim 1 wherein the positions defining a nucleic acid sequence of greater than 1000 base pairs define a nucleic acid sequence of between about 5,000 base pairs and about 100,000 base pairs in length.

12. The method of claim 1 wherein the positions defining a nucleic acid sequence of greater than 1000 base pairs define a nucleic acid sequence of between 7,000 base pairs and about 100,000 base pairs in length.

13. The method of claim 1 wherein the positions defining a nucleic acid sequence of greater than 1000 base pairs define a nucleic acid sequence of between 10,000 base pairs and about 100,000 base pairs in length.

14. The method of claim 1 wherein the positions defining a nucleic acid sequence of greater than 1000 base pairs define a nucleic acid sequence of between 8,000 base pairs and about 100,000 base pairs in length.

15. The method of claim 1 wherein the positions defining a nucleic acid sequence of greater than 1000 base pairs define a nucleic acid sequence of between 9,000 base pairs and about 100,000 base pairs in length.

16. The method of claim 1 wherein the positions defining a nucleic acid sequence of greater than 1000 base pairs define a nucleic acid sequence of between 20,000 base pairs and about 100,000 base pairs in length.

17. The method of claim 1 wherein the positions defining a nucleic acid sequence of greater than 1000 base pairs define a nucleic acid sequence of between 30,000 base pairs and about 100,000 base pairs in length.

18. The method of claim 1 wherein the positions defining a nucleic acid sequence of greater than 1000 base pairs define a nucleic acid sequence of between 40,000 base pairs and about 100,000 base pairs in length.

19. The method of claim 1 wherein the positions defining a nucleic acid sequence of greater than 1000 base pairs define a nucleic acid sequence of between 50,000 base pairs and about 100,000 base pairs in length.

20. The method of claim 1 wherein the Cas 9 protein is human codon optimized.

21. The method of claim 1 wherein the exogenous nucleic acid sequence is between about 2,000 base pairs and about 100,000 base pairs in length.

22. The method of claim 1 wherein the exogenous nucleic acid sequence is between about 3,000 base pairs and about 100,000 base pairs in length.

23. The method of claim 1 wherein the exogenous nucleic acid sequence is between about 4,000 base pairs and about 100,000 base pairs in length.

24. The method of claim 1 wherein the exogenous nucleic acid sequence is between about 5,000 base pairs and about 100,000 base pairs in length.

25. The method of claim 1 wherein the exogenous nucleic acid sequence is between about 6,000 base pairs and about 100,000 base pairs in length.

26. The method of claim 1 wherein the exogenous nucleic acid sequence is between about 7,000 base pairs and about 100,000 base pairs in length.

27. The method of claim 1 wherein the exogenous nucleic acid sequence is between about 8,000 base pairs and about 100,000 base pairs in length.

28. The method of claim 1 wherein the exogenous nucleic acid sequence is between about 9,000 base pairs and about 100,000 base pairs in length.

29. The method of claim 1 wherein the exogenous nucleic acid sequence is between about 10,000 base pairs and about 100,000 base pairs in length.

30. The method of claim 1 wherein the exogenous nucleic acid sequence is between about 20,000 base pairs and about 100,000 base pairs in length.

31. The method of claim 1 wherein the exogenous nucleic acid sequence is between about 30,000 base pairs and about 100,000 base pairs in length.

32. The method of claim 1 wherein the exogenous nucleic acid sequence of is between about 40,000 base pairs and about 100,000 base pairs in length.

33. The method of claim 1 wherein the exogenous nucleic acid sequence is between about 1,000 base pairs and about 10,000 base pairs in length.

34. The method of claim 1 wherein the exogenous nucleic acid sequence is between about 2,000 base pairs and about 10,000 base pairs in length.

* * * * *